(12) United States Patent
Shelton et al.

(10) Patent No.: US 11,882,994 B2
(45) Date of Patent: Jan. 30, 2024

(54) SYSTEMS AND METHODS FOR IMAGE RECONSTRUCTION AND ENDOSCOPIC TRACKING

(71) Applicant: GYRUS ACMI, INC., Westborough, MA (US)

(72) Inventors: Kurt G. Shelton, Bedford, MA (US); Sergey A. Bukesov, Acton, MA (US)

(73) Assignee: Gyrus ACMI, Inc., Westborough, MA (US)

( * ) Notice: Subject to any disclaimer, the term of this patent is extended or adjusted under 35 U.S.C. 154(b) by 265 days.

(21) Appl. No.: 17/378,436

(22) Filed: Jul. 16, 2021

(65) Prior Publication Data

US 2022/0028078 A1 Jan. 27, 2022

Related U.S. Application Data

(60) Provisional application No. 63/055,936, filed on Jul. 24, 2020.

(51) Int. Cl.
*A61B 1/00* (2006.01)
*A61B 5/06* (2006.01)
(Continued)

(52) U.S. Cl.
CPC ...... *A61B 1/000094* (2022.02); *A61B 1/0005* (2013.01); *A61B 1/00147* (2013.01);
(Continued)

(58) Field of Classification Search
CPC ......... G06T 2207/10068; G06T 7/0012; G06T 2207/10016; G06T 2207/30004; G06V 10/20; G06V 10/10; G06V 10/225
See application file for complete search history.

(56) References Cited

U.S. PATENT DOCUMENTS

| 6,554,824 B2 | 4/2003 | Davenport et al. |
| 9,017,316 B2 | 4/2015 | Khatchaturov et al. |

(Continued)

FOREIGN PATENT DOCUMENTS

| CN | 116249477 A | 6/2023 |
| DE | 112021003948 T5 | 5/2023 |

(Continued)

OTHER PUBLICATIONS

"International Application Serial No. PCT/US2021/042053, International Search Report dated Nov. 3, 2021", 5 pgs.

(Continued)

*Primary Examiner* — Guillermo M Rivera-Martinez
(74) *Attorney, Agent, or Firm* — Schwegman Lundberg & Woessner, P.A.

(57) ABSTRACT

Systems, devices, and methods for endoscopic mapping of a target and tracking of endoscope locations inside a subject's body during a procedure are disclosed. An exemplary system comprises an imaging system configured to capture an endoscopic image of the target that includes a footprint of an aiming beam directed at the target, and a video processor configured to identifying one or more landmarks from the captured endoscopic image and determine their respective locations relative to the aiming beam footprint, and generate a target map by integrating a plurality of endoscopic images based on landmarks identified from one or more of the plurality of endoscopic images. The target map can be used to track endoscope location during an endoscopic procedure.

30 Claims, 15 Drawing Sheets

(51) Int. Cl.
  *G06T 3/40* (2006.01)
  *G06T 3/60* (2006.01)
  *G06T 7/00* (2017.01)
  *A61B 5/00* (2006.01)
  *G06T 3/20* (2006.01)

(52) U.S. Cl.
  CPC .............. *A61B 5/0075* (2013.01); *A61B 5/06* (2013.01); *G06T 3/20* (2013.01); *G06T 3/4084* (2013.01); *G06T 3/60* (2013.01); *G06T 7/0014* (2013.01); *G06T 2207/10016* (2013.01); *G06T 2207/10068* (2013.01); *G06T 2207/20101* (2013.01); *G06T 2207/30004* (2013.01)

(56) References Cited

U.S. PATENT DOCUMENTS

| | | | |
|---|---|---|---|
| 9,445,871 | B2 | 9/2016 | Kang et al. |
| 9,486,286 | B2 | 11/2016 | Hodel et al. |
| 9,757,199 | B2 | 9/2017 | Chia et al. |
| 9,949,615 | B2 | 4/2018 | Zappia et al. |
| 9,968,403 | B2 | 5/2018 | Hasenberg et al. |
| 10,039,604 | B2 | 8/2018 | Chia et al. |
| 10,067,304 | B2 | 9/2018 | Yu et al. |
| 10,105,184 | B2 | 10/2018 | Beck et al. |
| 10,175,435 | B2 | 1/2019 | Peng et al. |
| 10,258,415 | B2 | 4/2019 | Harrah et al. |
| 10,383,690 | B2 | 8/2019 | Hodel et al. |
| 2005/0085717 | A1* | 4/2005 | Shahidi ............... A61B 8/4416 600/443 |
| 2009/0253991 | A1 | 10/2009 | Balas et al. |
| 2013/0070069 | A1* | 3/2013 | Hyde .................. G06T 7/0014 382/128 |
| 2013/0345509 | A1* | 12/2013 | Alamaro .......... A61B 1/000094 600/109 |
| 2015/0224249 | A1 | 8/2015 | Ciulla et al. |
| 2015/0230864 | A1 | 8/2015 | Xuan et al. |
| 2015/0272674 | A1 | 10/2015 | Xuan et al. |
| 2016/0081749 | A1 | 3/2016 | Zhang et al. |
| 2016/0166319 | A1 | 6/2016 | Yu et al. |
| 2018/0092693 | A1 | 4/2018 | Falkenstein et al. |
| 2019/0113700 | A1 | 4/2019 | Peng et al. |
| 2019/0151022 | A1 | 5/2019 | Yu et al. |
| 2019/0159839 | A1 | 5/2019 | Zhang et al. |
| 2019/0192237 | A1 | 6/2019 | Harrah et al. |
| 2019/0201136 | A1* | 7/2019 | Shelton, IV ........... G16H 50/20 |
| 2019/0231220 | A1* | 8/2019 | Refai .................... H04N 13/25 |
| 2019/0246908 | A1 | 8/2019 | Pyun et al. |
| 2019/0298449 | A1 | 10/2019 | Khachaturov et al. |
| 2019/0393669 | A1 | 12/2019 | Yu et al. |
| 2020/0281454 | A1* | 9/2020 | Refai ..................... A61B 90/39 |

FOREIGN PATENT DOCUMENTS

| | | |
|---|---|---|
| EP | 2020910 A2 | 2/2009 |
| EP | 2888988 A1 | 7/2015 |
| EP | 3510962 A1 | 7/2019 |
| EP | 3512448 A1 | 7/2019 |
| EP | 3522811 A1 | 8/2019 |
| WO | WO-1990014797 A1 | 12/1990 |
| WO | WO-2019157247 A1 | 8/2019 |
| WO | WO-2020033121 A1 | 2/2020 |
| WO | WO-2022020207 A1 | 1/2022 |

OTHER PUBLICATIONS

"International Application Serial No. PCT/US2021/042053, Written Opinion dated Nov. 3, 2021", 7 pgs.

"International Application Serial No. PCT/US2021/042053, International Preliminary Report on Patentability dated Feb. 2, 2023", 9 pgs.

* cited by examiner

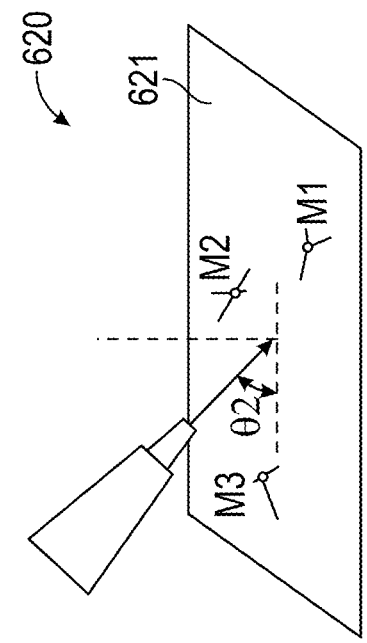
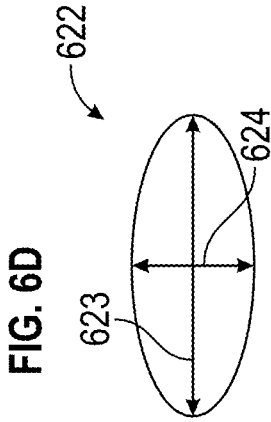
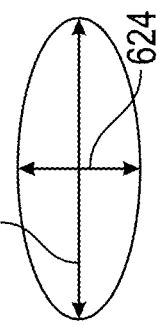
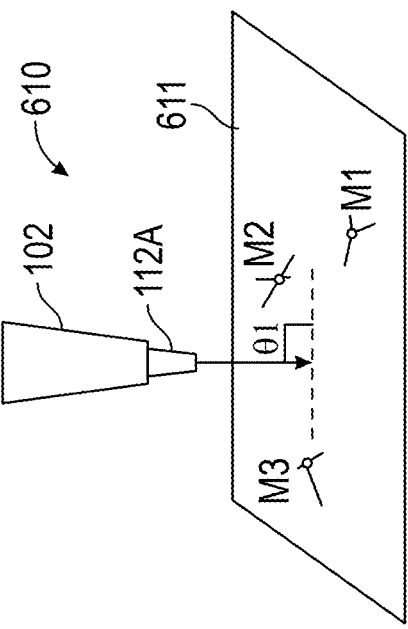
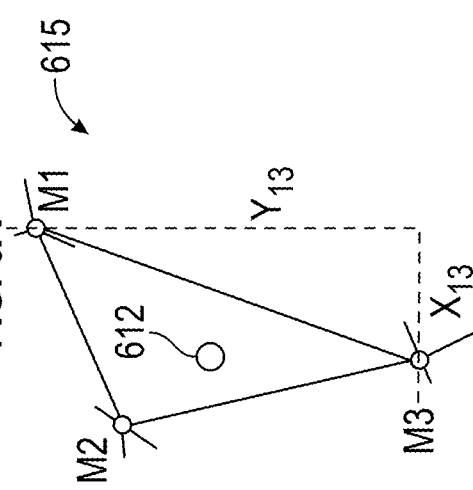
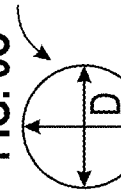

SYSTEMS AND METHODS FOR IMAGE RECONSTRUCTION AND ENDOSCOPIC TRACKING

CROSS-REFERENCE TO RELATED APPLICATION

This application claims priority to U.S. Provisional Patent Application Ser. No. 63/055,936, filed Jul. 24, 2020, the contents of which are incorporated herein by reference in their entirety.

TECHNICAL FIELD

This document relates generally to endoscopy, and more specifically relates to systems and methods for endoscopic mapping of a target and tracking the endoscope location during a procedure.

BACKGROUND

Endoscopes are typically used to provide access to an internal location of a subject such that a physician is provided with visual access. An endoscope is normally inserted into a patient's body, delivers light to a target (e.g., a target anatomy or object) being examined, and collects light reflected from the object. The reflected light carries information about the object being examined and can be used to create an image of the object. Some endoscopes include a working channel through which the operator can perform suction or pass instruments such as brushes, biopsy needles or forceps, or perform minimally invasive surgery to remove unwanted tissue or foreign objects from the body of the patient.

Some endoscopes include, or may be used together with, a laser or plasma system for delivering surgical laser energy to a target anatomy or object, such as soft or hard tissue. Examples of the laser therapy include ablation, coagulation, vaporization, fragmentation, etc. In lithotripsy applications, laser has been used to break down calculi structures in kidney, gallbladder, ureter, among other stone-forming regions, or to ablate large calculi into smaller fragments.

Video systems have been used to assist a physician or technician to visualize the procedure site and navigate the endoscope during an endoscopic procedure. An image-guided endoscopy generally requires localizing endoscope location and tracking endoscope motion in a coordinate system of the target region. An accurate mapping of the target region and efficient endoscope localization and tracking may improve precision of endoscope maneuvering during an endoscopic procedure, enhance the interventional capabilities of the physician or technician, and improve therapy (e.g., laser therapy) efficacy.

SUMMARY

The present document describes systems, devices, and methods for endoscopic mapping of a target and tracking of endoscope locations inside a subject's body during a procedure. An exemplary system comprises an imaging system configured to capture an endoscopic image of the target that includes a footprint of an aiming beam directed at the target, and a video processor configured to identifying one or more landmarks from the captured endoscopic image and determine their respective locations relative to the aiming beam footprint, and generate a target map by integrating a plurality of endoscopic images based on landmarks identified from one or more of the plurality of endoscopic images. The target map can be used to track endoscope location during an endoscopic procedure.

Example 1 is a system for endoscopic mapping of a target. The system comprising: an imaging system configured to capture an endoscopic image of the target, the endoscopic image including a footprint of an aiming beam directed at the target; and a video processor configured to: identifying one or more landmarks from the captured endoscopic image and determine their respective locations relative to the aiming beam footprint; and generate a target map by integrating a plurality of endoscopic images based on landmarks identified from one or more of the plurality of endoscopic images.

In Example 2, the subject matter of Example 1 optionally includes the video processor that can be configured to identify a tissue type at a location of the aiming beam, and to mark the aiming beam footprint with a visual identifier indicating the identified tissue type.

In Example 3, the subject matter of any one or more of Examples 1-2 optionally includes a spectrometer communicatively coupled to the video processor, the spectrometer configured to measure one or more spectroscopic properties of an illuminating light signal reflected from the target; wherein the video processor is configured to identify a tissue type at a location of the aiming beam based on the one or more spectroscopic properties, and to mark the aiming beam footprint with a visual identifier indicating the identified tissue type.

In Example 4, the subject matter of any one or more of Examples 2-3 optionally includes the video processor that can be configured to identify the tissue type as normal tissue or abnormal tissue.

In Example 5, the subject matter of any one or more of Examples 2-4 optionally includes the video processor that can be configured to mark the aiming beam footprint with different colors to indicate different tissue types.

In Example 6, the subject matter of any one or more of Examples 1-5 optionally includes the video processor that can be configured to identify the one or more landmarks from the endoscopic image based on variation in brightness of pixels of the endoscopic image.

In Example 7, the subject matter of Example 6 optionally includes the one or more landmarks that are represented in the endoscopic image as a line segment or intersected line segments.

In Example 8, the subject matter of any one or more of Examples 1-7 optionally includes the video processor that can be configured to: select, from the landmarks identified from one or more of the plurality of endoscopic images, a subset of landmarks based on whether laser energy is activated at respective target sites where the identified landmarks are located; and generate the target map by integrating the plurality of endoscopic images based on the selected subset of landmarks.

In Example 9, the subject matter of any one or more of Examples 1-8 optionally includes the plurality of endoscopic images that can include images of various sites of the target including a first endoscopic image of a first target site captured from a first endoscopic location and a second endoscopic image of a second target site captured from a second endoscopic location, where the video processor is configured to: identify matching landmarks including two or more landmarks in the first endoscopic image that match corresponding two or more landmarks in the second endoscopic image; align the first and second endoscopic images with respect to the matching landmarks in a coordinate system of the first image; and generate the target map using at least the aligned first and second images.

In Example 10, the subject matter of Example 9 optionally includes the video processor that can be configured to: transform the second image including one or more of a scaling, a translation, or a rotation of the second image; and align the transformed second image and the first image with respect to the matching landmarks.

In Example 11, the subject matter of Example 10 optionally includes the transformation of the second image that can include a matrix multiplication by a transformation matrix.

In Example 12, the subject matter of any one or more of Examples 10-11 optionally includes the video processor that can be configured to scale the second image using a scaling factor based on a ratio of a distance between two of the matching landmarks in the first image to a distance between the corresponding two landmarks in the second image.

In Example 13, the subject matter of any one or more of Examples 10-12 optionally includes the video processor that can be configured to scale the second image by a scaling factor based on a ratio of a geometric feature of an aiming beam footprint in the first image to a geometric feature of an aiming beam footprint in the second image.

In Example 14, the subject matter of any one or more of Examples 10-13 optionally includes the video processor that can be configured to transform the second image to correct for a change in endoscopic orientations between the first and second images, the endoscopic orientation indicating a tilt of an endoscope tip with respect to a target site.

In Example 15, the subject matter of Example 14 optionally includes the video processor that can be configured to detect the change in endoscopic orientation using a first slope between two of the matching landmarks in the first image and a second slope between the corresponding two landmarks in the second image.

In Example 16, the subject matter of any one or more of Examples 14-15 optionally includes the video processor that can be configured to detect the change in endoscopic orientation using a first geometric feature of an aiming beam footprint in the first image and a second geometric feature of an aiming beam footprint in the second image.

In Example 17, the subject matter of Example 16 optionally includes at least one of the first or second aiming beam footprint that may have an elliptical shape with a major axis and a minor axis, and at least one of the first or the second geometric feature that can a ratio of a length of the major axis to a length of the minor axis.

In Example 18, the subject matter of any one or more of Examples 1-17 optionally includes an endoscopic tracking system configured to: from a real-time image of a procedure site of the target captured by the imaging system from an unknown endoscopic location during an endoscopic procedure, identify matching landmarks including two or more landmarks in the target map that match corresponding two or more landmarks in the real-time image; register the real-time image to the target map using the matching landmarks; and track endoscope tip location based on the registration of the real-time image.

In Example 19, the subject matter of Example 18 optionally includes the endoscopic tracking system that can be configured to identify the matching landmarks based on one or more ratios of distances between landmarks in the real-time image and one or more ratios of distances between landmarks in the target map.

In Example 20, the subject matter of any one or more of Examples 18-19 optionally includes the endoscopic tracking system that can be configured to generate an indication of a change in tissue type at a target site.

Example 21 is a method for endoscopic mapping of a target. The method comprises: directing an aiming beam at a target; capturing an endoscopic image of the target via an imaging system, the endoscopic image including a footprint of the aiming beam; identifying, via a video processor, one or more landmarks from the captured endoscopic image, and determining respective locations of the one or more landmarks relative to the aiming beam footprint; and generating, via the video processor, a target map by integrating a plurality of endoscopic images based on landmarks identified from one or more of the plurality of endoscopic images.

In Example 22, the subject matter of Example 21 optionally includes identifying a tissue type at a location of the aiming beam using an illuminating light signal reflected from the target, and marking the aiming beam footprint with a visual identifier indicating the identified tissue type.

In Example 23, the subject matter of any one or more of Examples 21-22 optionally includes identifying the one or more landmarks from the endoscopic image based on variation in brightness of pixels of the endoscopic image.

In Example 24, the subject matter of any one or more of Examples 21-23 optionally includes, wherein the plurality of endoscopic images include images of various sites of the target including a first endoscopic image of a first target site captured at a first endoscopic location and a second endoscopic image of a second target site captured at a second endoscopic location, the method comprising: identifying matching landmarks including two or more landmarks in the first endoscopic image that match corresponding two or more landmarks in the second endoscopic image; aligning the first and second endoscopic images with respect to the matching landmarks in a coordinate system of the first image; and generating the target map using at least the aligned first and second images.

In Example 25, the subject matter of Example 24 optionally includes aligning the first and second endoscopic images including: transforming the second image including one or more of a scaling, a translation, or a rotation of the second image; and aligning the transformed second image and the first image with respect to the matching landmarks.

In Example 26, the subject matter of Example 25 optionally includes transforming the second image, including scaling the second image by a scaling factor based on a ratio of a distance between two of the matching landmarks in the first image to a distance between the two corresponding landmarks in the second image.

In Example 27, the subject matter of any one or more of Examples 25-26 optionally includes transforming the second image, including scaling the second image by a scaling factor based on a ratio of a geometric feature of an aiming beam footprint in the first image to a geometric feature of an aiming beam footprint in the second image.

In Example 28, the subject matter of any one or more of Examples 25-27 optionally includes transforming the second image, including correcting for a change in endoscopic orientation between the first and second images, the endoscopic orientation indicating a tilt of an endoscope tip with respect to a target site.

In Example 29, the subject matter of Example 28 optionally includes detecting the change in endoscopic orientation using a first slope between two of the matching landmarks in the first image and a second slope between the corresponding two landmarks in the second image.

In Example 30, the subject matter of any one or more of Examples 28-29 optionally includes detecting the change in endoscopic orientation using a first geometric feature of an aiming beam footprint in the first image and a second geometric feature of an aiming beam footprint in the second image.

In Example 31, the subject matter of any one or more of Examples 21-30 optionally includes: capturing a real-time image of a procedure site of the target using the imaging system from an unknown endoscopic location during an endoscopic procedure; identifying matching landmarks including two or more landmarks in the target map that match corresponding two or more landmarks in the real-time image; registering the real-time image to the target map using the matching landmarks; and tracking endoscope tip location based on the registration of the real-time image.

In Example 32, the subject matter of Example 31 optionally includes identifying matching landmarks based on one or more ratios of distances between landmarks in the real-time image and one or more ratios of distances between landmarks in the target map.

Example 33 is at least one non-transitory machine-readable storage medium that includes instructions that, when executed by one or more processors of a machine, cause the machine to perform operations comprising: directing an aiming beam at a target; capturing an endoscopic image of the target, the endoscopic image including a footprint of the aiming beam; identifying one or more landmarks from the captured endoscopic image, and determining respective locations of the one or more landmarks relative to the aiming beam footprint; and generating a target map by integrating a plurality of endoscopic images based on landmarks identified from one or more of the plurality of endoscopic images.

In Example 34, the subject matter of Example 33 optionally includes, wherein the instructions cause the machine to perform operations further comprising: identifying a tissue type at a location of the aiming beam; and marking the aiming beam footprint with a visual identifier indicating the identified tissue type.

In Example 35, the subject matter of any one or more of Examples 33-34 optionally includes, wherein the instructions cause the machine to perform operations further comprising identifying the one or more landmarks from the endoscopic image based on variation in brightness of pixels of the endoscopic image.

In Example 36, the subject matter of any one or more of Examples 33-35 optionally includes, wherein the plurality of endoscopic images include images of various sites of the target including a first endoscopic image of a first target site captured at a first endoscopic location and a second endoscopic image of a second target site captured at a second endoscopic location, and wherein the instructions cause the machine to perform operations further comprising: identifying matching landmarks including two or more landmarks in the first endoscopic image that match corresponding two or more landmarks in the second endoscopic image; aligning the first and second images with respect to the matching landmarks in a coordinate system of the first image; and generating the target map using at least the aligned first and second images.

In Example 37, the subject matter of Example 36 optionally includes, wherein the operation of aligning the first and second endoscopic images includes: transforming the second image including one or more of a scaling, a translation, or a rotation of the second image; and aligning the transformed second image and the first image with respect to the matching landmarks.

In Example 38, the subject matter of Example 37 optionally includes, wherein the operation of transforming the second image includes scaling the second image by a scaling factor based on a ratio of a distance between two of the matching landmarks in the first image to a distance between the two corresponding landmarks in the second image.

In Example 39, the subject matter of any one or more of Examples 37-38 optionally includes, wherein the operation of transforming the second image includes scaling the second image by a scaling factor based on a ratio of a geometric feature of an aiming beam footprint in the first image to a geometric feature of an aiming beam footprint in the second image.

In Example 40, the subject matter of any one or more of Examples 37-39 optionally includes, wherein the operation of transforming the second image includes correcting for a change in endoscopic orientation between the first and second images, the endoscopic orientation indicating a tilt of an endoscope tip with respect to a target site.

In Example 41, the subject matter of Example 40 optionally includes, wherein the instructions cause the machine to perform operations further comprising detecting the change in endoscopic orientation using a first slope between two of the matching landmarks in the first image and a second slope between the corresponding two landmarks in the second image.

In Example 42, the subject matter of any one or more of Examples 40-41 optionally includes, wherein the instructions cause the machine to perform operations further comprising detecting the change in endoscopic orientation using a first geometric feature of an aiming beam footprint in the first image and a second geometric feature of an aiming beam footprint in the second image.

In Example 43, the subject matter of any one or more of Examples 33-42 optionally includes, wherein the instructions cause the machine to perform operations further comprising: capturing a real-time image of a procedure site of the target from an unknown endoscopic location during an endoscopic procedure; identifying matching landmarks including two or more landmarks in the target map that match corresponding two or more landmarks in the real-time image; registering the real-time image to the target map using the matching landmarks; and tracking endoscope tip location based on the registration of the real-time image.

In Example 44, the subject matter of any one or more of Examples 33-43 optionally includes, wherein the operation of identifying matching landmarks is based on one or more ratios of distances between landmarks in the real-time image and one or more ratios of distances between landmarks in the target map.

This summary is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

FIGS. 6A-6F are diagrams illustrating by way of example effects of endoscopic orientation on endoscopic image features, and correction for a change in endoscopic orientation from one endoscopic image to another.

DETAILED DESCRIPTION

Figure 1:
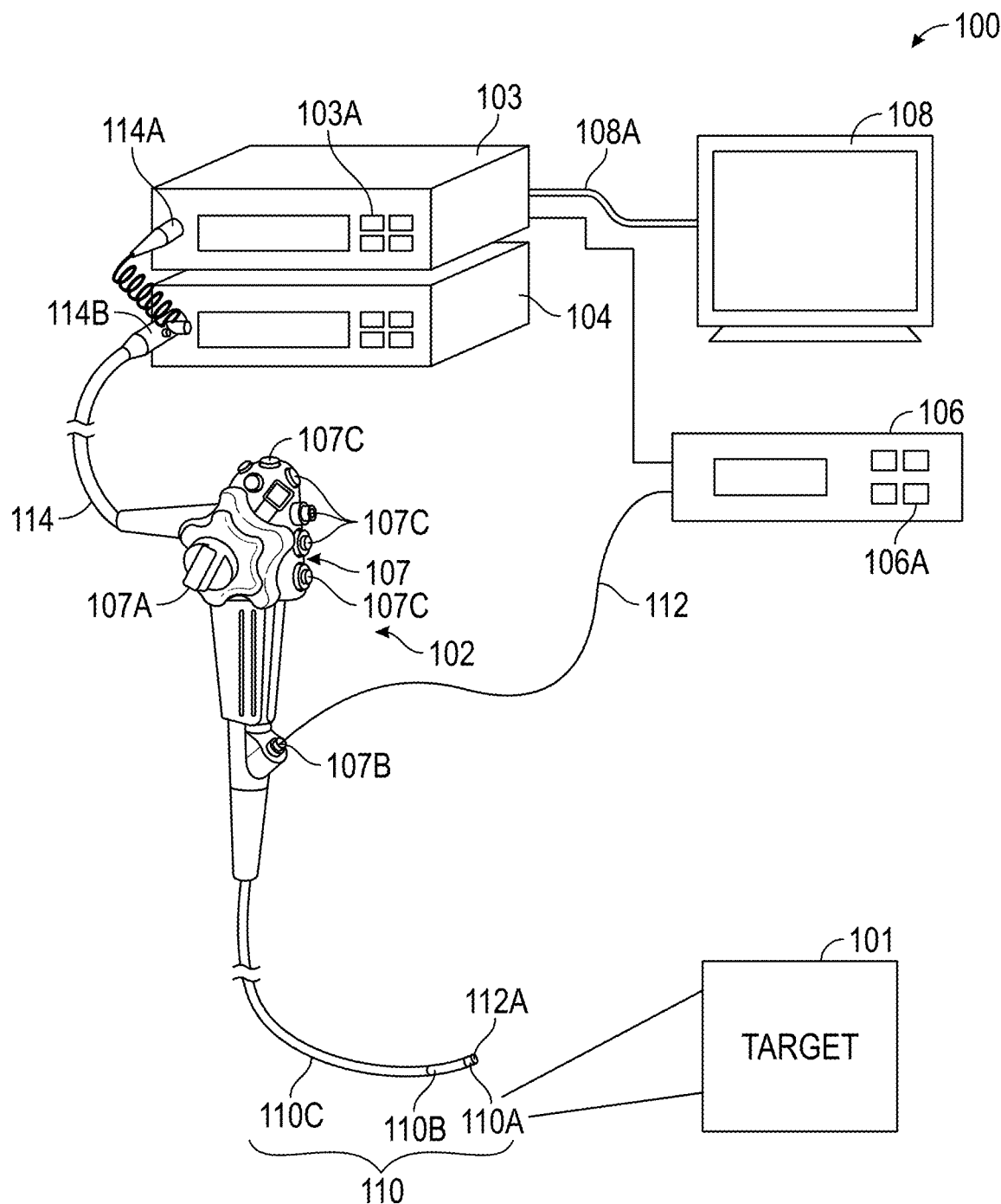
FIG. 1 is a diagram illustrating an example of a medical system for use in an endoscopic procedure.

Minimally invasive endoscopic surgery is a surgical procedure in which a rigid or flexible endoscope is introduced into a target region of a subject's body through a natural orifice or a small incision in the skin. Additional surgical tools, such as a laser fiber, can be introduced into the subject's body through similar ports with the endoscope being used to provide a visual feedback to a surgeon of the surgical site and the surgical tools.

An endoscopic surgery may include a pre-operative phase and an intra-operative phase. The pre-operative phase involves acquiring images or video frames of a target anatomy or object using an imaging system (e.g., a video camera), and reconstructing a map using the images or video frames. The map may be used for diagnostic evaluation or for endoscopic procedure planning. During the intra-operative phase, an endoscope can be introduced into a procedure site of the target. An operator may move and pivot the endoscope distal tip, and acquire real-time images of the procedural site via an imaging system such as located at the endoscope distal tip. Position and orientation of a surgical tool (e.g., a laser fiber) at the endoscopic distal tip can be monitored and tracked throughout the procedure.

One conventional intra-operative tracking involves a freehand technique, whereby a surgeon views the surgical field on a monitor that displays realtime images or video of the surgical field without an automated tracking or navigation system. This approach fails to establish a relationship between the images that facilitates a tracking of the positions and orientations of an endoscopic surgical tool relative to the target. Another approach involves a navigation-based tracking system, such as an optical or electromagnetic tracking system, that tracks the positions and orientations of the endoscopic surgical took. An image registration procedure can be performed to align the real-time images with the target map. Fiducial markers, which are visible on real-time images, are used as references to guide a surgeon with real-time feedback of positions and orientations of endoscopic surgical tools. The fiducial markers can be external objects attached to the patient, or internal anatomical fiducials. External fiducials may lack in consistency of location, and increase system complexity. The use of internal fiducials generally put restrictions on physical movement of the endoscope, such as requiring the scope to touch anatomical fiducials during the procedure, which may extend procedure time. Conventional navigation-based endoscopic tracking system may also suffer from degraded tracking performance in the presence of image distortion or deformation, such as due to changes in camera positions, viewing directions, and orientations (e.g., title or skew) with respect to target surface. For at least those reasons stated above, the present inventors have recognized an unmet need for an improved endoscopic mapping and tracking system that is more robust to image distortion or deformation when used in an endoscopic procedure.

Described herein are systems, devices, and methods for endoscopic mapping of a target and tracking endoscope location inside a subject's body during a procedure. An exemplary system comprises an imaging system configured to capture an endoscopic image of the target that includes a footprint of an aiming beam directed at the target, and a video processor configured to identifying one or more landmarks from the captured endoscopic image and determine their respective locations relative to the aiming beam footprint, and generate a target map by integrating a plurality of endoscopic images based on landmarks identified from one or more of the plurality of endoscopic images. The target map can be used to track endoscope location during a procedure during a procedure.

The systems, devices, and methods according to various embodiments discussed herein can provide improved endoscopic mapping of a target and tracking of endoscope location during an endoscopic procedure. In accordance with various examples of the present disclosure, various image features may be generated from endoscopic images including, for example, landmarks and their locations with respect to aiming beam footprints, inter-landmark spatial relations, shapes and geometric properties of aiming beam footprints, among others. Image registration, reconstruction of a target map, and endoscopic tracking based on those image features described herein are more resilient to image rotation, magnification, shrinkage, changes in camera positions, viewing directions, or a change in endoscope orientation during an endoscopic procedure. With improved navigation and endoscopic tracking, an operator's interventional capabilities and precision of endoscope operation can be enhanced, the procedure time can be reduced, and overall procedure effectiveness, patient safety, and system reliability can be improved.

The subject matter discussed in this document may be applied to various endoscopic applications including, but are not limited to, an arthroscopy, bronchoscopy, a colonoscopy, a laparoscopy, a brain endoscopy, and an endoscopic cardiac surgery. Examples of an endoscopic cardiac surgery include, but are not limited to, endoscopic coronary artery bypass, endoscopic mitral and aortic valve repair and replacement. In this document, the "endoscopic" is broadly defined herein as a characterization of images acquired by any type of endoscope having the ability to image from inside a body.

Examples of an endoscope for purposes of the present invention include, but are not limited to, any type of scope, flexible or rigid (e.g., endoscope, arthroscope, bronchoscope, choledochoscope, colonoscope, cystoscope, duodenoscope, gastroscope, hysteroscope, laparoscope, laryngoscope, neuroscope, otoscope, push enteroscope, rhinolaryngoscope, sigmoidoscope, sinuscope, thorascope, etc.) and any device similar to a scope that is equipped with an image system (e.g., a nested cannula with imaging). The imaging is local, and surface images may be obtained optically with fiber optics, lenses, or miniaturized (e.g. CCD based) imaging systems. Examples of fluoroscope for purposes of the present invention include, but are not limited to, an X-ray imaging system.

Figure 2:
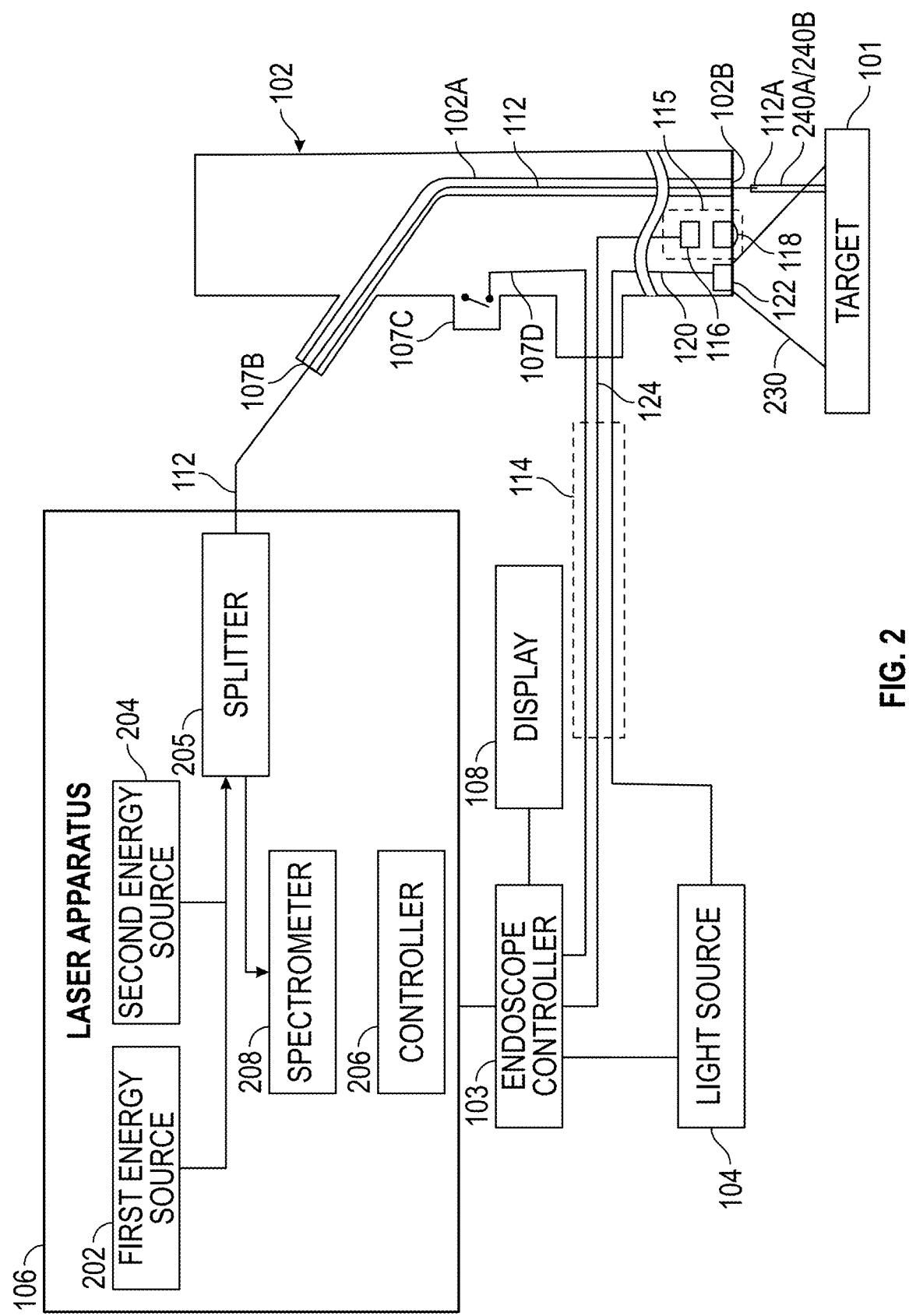
FIG. 2 is schematic diagram of portions of the system as shown in FIG. 1.

FIG. 1 is a diagram illustrating an example of a medical system 100 for use in an endoscopic procedure. The system 100 comprises an endoscope 102, an endoscope controller 103, a light source 104, a laser apparatus 106 and a display 108. A schematic diagram of portions of the system 100 is illustrated in FIG. 2. The endoscope 102 can include an insertion portion 110 at a distal portion and an operating unit 107 at a proximal portion of the endoscope 102. The insertion portion 110 can be configured to be inserted into a target site of a subject, capture an image of a target 101, and optionally perform a procedure therein. The insertion portion 110 can be formed using a lighting fiber (light guide), an electric cable, an optical fiber, or the like. In an example as illustrated in FIG. 1, the insertion portion 110 includes a distal end portion 110a incorporating an imaging unit, a bendable bend portion 110b including a plurality of bend pieces, and a flexible tube portion 110c provided on a proximal end portion side of the bend portion 110b, which is flexible.

Referring to FIG. 2, the distal end portion 110a may be provided with a light guide 120 configured to be coupled to the light source 104 and project illumination light 230 onto the target 101 via an illumination lens 122. The distal end portion 110a may include an observation unit, such as an imaging system 115 configured to image the target 101. The imaging system 115 can include an image sensor 116 and associated lens system 118. Examples of the image sensor 116 can include a CCD or CMOS camera sensitive in ultraviolet (UV), visible (VIS) or infrared (IR) wavelengths. The endoscope 102 may include an insertion port 107b coupled to a treatment tool channel 102a located inside the endoscope 102 and extending along the insertion portion 110. An optical pathway 112, disposed within the channel 102a through the insertion port 107b, has a proximal end operatively connected to the laser apparatus 106, and extend distally from a distal end opening 102b of the channel 102a. Laser energy, such as a treatment beam 240a or an aiming beam 240b, may be transmitted through an optical pathway 112, and emitted from the distal tip 112a of the optical pathway 112 and directed at the target 101. The endoscope 102 may optionally include an air/water supply nozzle (not illustrated) at the distal end portion 110a.

The operating unit 107 can be configured to be held by an operator. The operating unit 107 may be located at a proximal end portion of the endoscope 102, and is configured to in communication with the endoscope controller 103 and the light source 104 via a flexible universal cord 114 extended from the operating unit 107. As illustrated in FIG. 1, the operating unit 107 includes a bending knob 107a for bending the bend portion 110b in the up and down direction and the right and left direction, the treatment tool insertion port 107b through which a treatment tool, such as medical forceps or the optical pathway 112 is inserted into a body cavity of the subject, and a plurality of switches 107c for operating a peripheral device such as the endoscope controller 103, the light source 104, an air supply device, a water supply device, or a gas supply device. The treatment tool, such as the optical pathway 112, may be inserted from the treatment tool insertion port 107b and through the channel 102a such that a distal end thereof is exposed from an opening 102b (see FIG. 2) of the channel 102a at the distal end of the insertion portion 110.

The endoscope controller 103 can control operations of one or more elements of the system 100, such as the light source 104, the laser apparatus 106, or the display 108 that displays an image of the target 101 based on the image or video signal sensed by the image sensor 116. The distal tip of the endoscope 102 may be positioned and oriented such that the aiming beam 240b is directed at a target location within the field of view (FOV) of the imaging system 115; and that the endoscopic image includes a footprint of the aiming beam 240b. Although the aiming beam 240b is shown as a laser beam emitted from a laser energy source, other light sources may be used to produce an aiming beam that travels along an optical fiber. The endoscope controller 103 can apply image processing to the endoscopic image, and reconstruct a map of the target by integrating multiple endoscopic images. In some examples, the endoscope controller 103 can use the reconstructed target map to localize and track endoscope tip during an endoscopic procedure. Examples of the endoscope controller 103, including endoscopic mapping of the target and tracking of endoscopic locations, are discussed below such as with reference to FIG. 3.

The universal cord 114 includes a lighting fiber, a cable, or the like. The universal cord 114 may be branched at the proximal end thereof. One end of the branched ends is a connector 114a, and the other proximal end of the branched ends is a connector 114b. The connector 114a is attachable/detachable to/from a connector of the endoscope controller 103. The connector 114b is attachable/detachable to/from the light source 104. The universal cord 114 propagates the illumination light from the light source 104 to the distal end portion 110a via the connector 114b and the light guide 120. Further, the universal cord 114 can transmit an image or video signal captured by the imaging system 115 to the endoscope controller 103 via a signal line 124 (see FIG. 2) in the cord and via the connector 114a. The endoscope controller 103 executes image processing of the image or video signal output from the connector 114a, and controls at least part of the components making up the system 100.

The light source 104 can generate illumination light while the endoscope 102 is being used in a procedure. The light source 104 can include, for example, a Xenon lamp, a light-emitting diode (LED), a laser diode (LD), or any combination thereof. In an example, the light source 104 may include two or more light sources that emit light having different illumination characteristics, referred to as illumination modes. Under the control of the endoscope controller 103, the light source 104 emits light, supplies the light to the endoscope 102 connected via the connector 114b and the light guide of the universal cord 114 as illumination light for the inside of the subject as an object. The illumination modes may be a white light illumination mode or a special light illumination mode, such as a narrow band imaging mode, an auto fluorescence imaging mode or an infrared imaging mode. A special light illumination can concentrate and intensify specific wavelengths of light, for example, resulting in a better visualization of a superficial microvessel and mucosal surface structures to enhance the subtle contrast of the irregularities of the mucosa.

The display 108 includes, for example, a liquid crystal display, an organic electro-luminescence display, or the like. The display 108 can display information including the endoscopic images of the target subject to image processing by the endoscope controller 103 via a video cable 108a. In some examples, one or more of endoscopic images may each include a footprint of the aiming beam 240b. An operator may observe and track behavior of the endoscope inside the subject by operating the endoscope 102 while watching the image displayed on the display 108.

The laser apparatus 106 is for use with the optical pathway 112, such as a laser fiber. Referring to FIG. 2, the laser apparatus 106 can include one or more energy sources, such as a first energy source 202 and a second energy source 204, for generating laser energy coupled to the proximal end of the optical pathway 112. In an example, a user may select an energy source, such as via a button 106a on the laser apparatus 106 (see FIG. 1) or a foot switch (not shown), through software or a user interface on the display 108 or other inputs, manual or automatic as are known in the art.

The first energy source 202 may be optically coupled to the optical pathway 112 and configured to deliver treatment beam 240a to the target 101 through the optical pathway 112. By way of example and not limitation, the first energy source 202 can include a thulium laser, used to generate laser light for delivery through the optical pathway 112 to the target tissue to operate in different treatment modes, such as a cutting (ablation) mode and a coagulation (hemostasis) mode. Other energy sources known in the art for such treatment of tissue, or any other treatment modes, can also be used for the first energy source 202, such as Ho:YAG, Nd:YAG and $CO_2$ as well as others known in the art.

The second energy source 204 may be optically coupled to the optical pathway 112 and configured to direct an aiming beam 240b at the target 101 through the optical pathway 112. Although the aiming beam 240b is shown as a laser beam emitted from a laser source, other light sources may be used to produce an aiming beam 240b that travels along an optical fiber. The aiming beam 240b may be emitted when the target is illuminated by the illuminated light 230. In some examples, the second energy source 204 may emit at least two different aiming beams, where the first aiming beam has at least one characteristic different from the second aiming beam. Such differing characteristics can include wavelength, power level and/or emitting pattern. For example, the first aiming beam can have a wavelength in the range of 500 nm to 550 nm while the second aiming beam can have a wavelength in the range of 635 nm to 690 nm. The characteristics of the different aiming beams may be selected based on the visibility of the aiming beams in the image processed by the endoscope controller 103 and displayed on the display 108 under certain illumination modes provided by the light source 104.

The laser apparatus 106 may include a controller 206 comprising hardware, such as a microprocessor, that controls the operation of the first and second energy sources 202 and 204. In an example as illustrated in FIG. 2, in response to the illumination light 230, light reflected from the target 101 may enter into the optical pathway 112 from the distal tip 112a. The optical pathway 112, which is configured to transmit laser beams, may also be used as a pathway to transmit the reflected light back to the laser apparatus 106. A splitter 205 may collect the reflected light, split it from the laser beams delivered to the target 101 via the same optical pathway 112. The laser apparatus 106 can include a spectrometer 208 operatively coupled to the splitter 205 and configured to detect the reflected light out of the splitter. Alternatively, the reflected light may be guided through an optical pathway (e.g., an optical fiber) separated from the optical pathway 112. The spectrometer 208 can operatively be coupled to the dedicated optical pathway and detect reflected light therefrom.

The spectrometer 208 can measure one or more spectroscopic properties from the sensed reflected signal. Examples of the spectrometer 208 may include a Fourier Transform Infrared (FTIR) spectrometer, a Raman spectrometer, a UV-VIS spectrometer, a UV-VIS-IR spectrometer, or a fluorescent spectrometer, among others. The spectroscopic properties may include characteristics such as reflectivity, reflectance spectrum, absorption index, and the like. The spectroscopic properties may be indicative of a structure category (e.g., anatomical tissue or calculi) or specific structure types indicative of chemical composition of the target.

Figure 3:
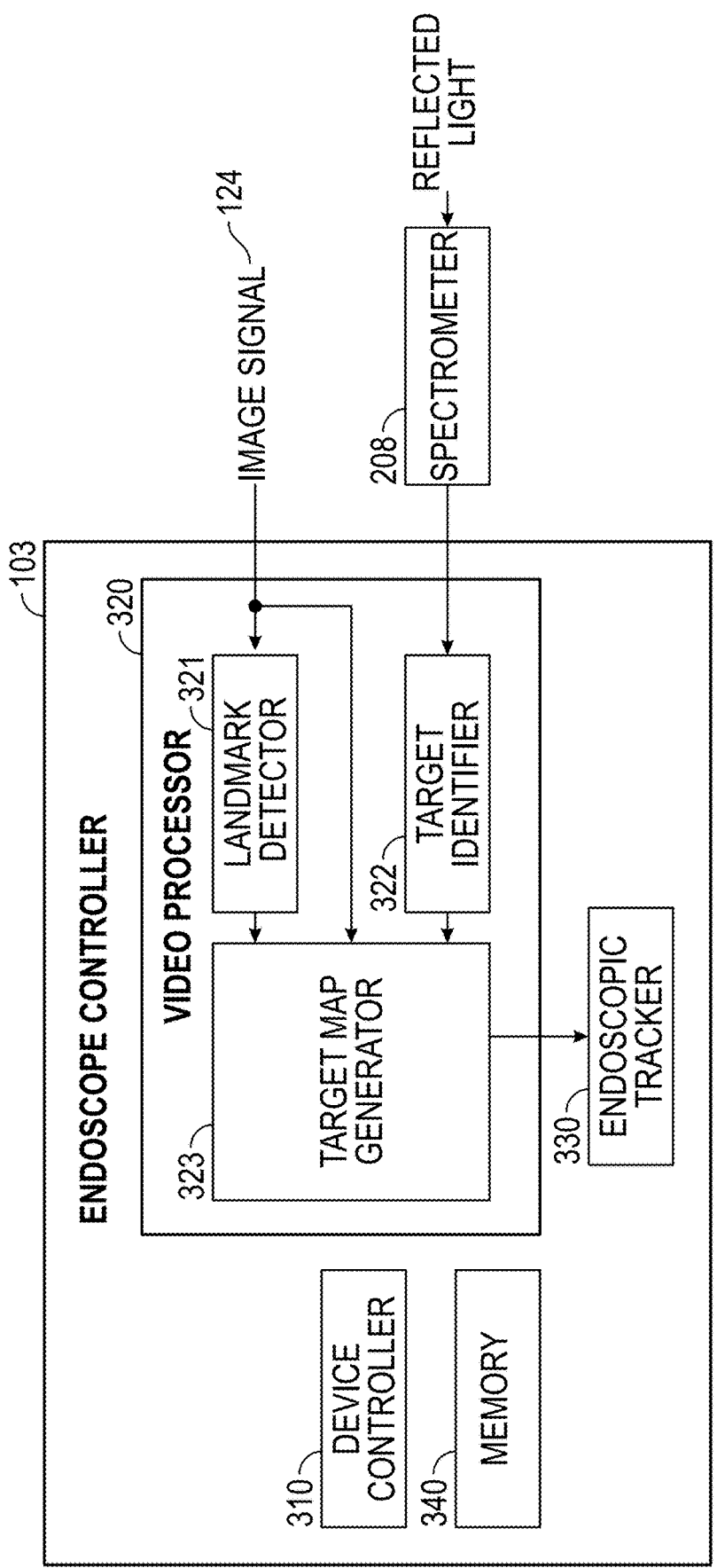
FIG. 3 is a block diagram illustrating an example of an endoscope controller for controlling various parts of the system as shown in FIG. 1.

FIG. 3 is a block diagram illustrating an example of the endoscope controller 103 for use in the system 100. The endoscope controller 103 comprises hardware, such as a microprocessor, for performing operations according to various examples as described herein. The endoscope controller 103 can include a device controller 310, a video processor 320, an endoscopic tracker 330, and a memory 340. The device controller 310 can control operations of one or more components of the system 100 such as the endoscope 102, the display 108, the light source 104, or the laser apparatus 106.

The video processor 320 may receive an image or video signal from the imaging system 115 through the signal line 124, and process the image or video signal to generate an image or a video frame that may be displayed on the display 108. In some examples, a plurality of endoscopic images (e.g., video frames) may be generated and displayed on the display 108. The plurality of endoscopic images may be taken at the same site of the target 101 when the endoscope tip and the imaging system 115 remain stationary, while the distal tip 112a of the optical pathway 112 (e.g., a laser fiber) may move and direct the laser beam to different locations of the target. In some examples, the plurality of endoscopic images of the same target site may be taken at different times. An image taken at a later time may be registered with a previously taken image of the same target site, such as through a process of image transformant and/or image alignment. The registered images may be used to determine a change in tissue status at the target site. Additionally or alternatively, the plurality of endoscopic images may be taken at different sites of the target 101, such as when the endoscope distal tip pans across the target 101. During endoscope panning, the endoscope distal tip may be moved and positioned at different endoscopic locations $\{L_1, L_2, \ldots, L_N\}$ (i.e., the locations of the endoscope distal tip), either manually by an operator or automatically by an endoscope actuator. The imaging system 115, under the control of the endoscope controller 103, can take a sequence of images (or video frames) $\{G_1, G_2, \ldots, G_N\}$ at respective target sites $\{S_1, S_2, \ldots S_N\}$ that jointly cover a substantial surface area of the target 101. For example, an endoscopic image $G_i$ of a target site $S_i$ that falls within the FOV of imaging system 115 may be taken when the lens system 118 is positioned and oriented at an endoscopic location $L_i$. As the endoscope distal tip is moved to a different endoscopic location $L_j$, another endoscopic image $G_j$ may be taken at a different target site $S_j$ that falls within the FOV of the imaging system 115. The video processor 320 may integrate the resulting images $\{G_1, G_2, \ldots, G_N\}$ to create a map for the target 101, such as in accordance with various examples as discussed further below such as with reference to FIGS. 4A-4F and 5.

As discussed above, the endoscope tip may be positioned and oriented such that the aiming beam 240b falls within the FOV of the imaging system 115, and a aiming beam footprint may be captured in the endoscopic image (e.g., $G_i$). In an example, the video processor 320 may tint the aiming beam footprint with a color different from the background of the endoscopic image. The video processor 320 can identify the location where the aiming beam 240b is currently illuminating by matching the color of the aiming beam 240b to the color of pixels of the endoscopic image.

The video processor 320 may include a landmark detector 321 configured to detect one or more landmarks from an endoscopic image. The landmarks may be manually created by an operator, or automatically identified using an image processing algorithm. In an example, the landmark detector 321 may detect landmarks based on variation in brightness of the pixels of the endoscopic image. In an example, the landmark detector 321 may detect landmarks using edge detection constrained by a minimum contrast threshold, and number of pixels between similar positive and negative contrast slopes. The detected landmarks may indicate blood vessels. An edge detection may involve detecting a light-to-dark transition of pixel brightness indicative of a start of a blood vessel segment, and a subsequent dark-to-light transition of pixel brightness indicative of an end of the blood vessel segment. Additional criteria may be applied to confirm the detection of the blood vessel. For example, if said subsequent transition occurs with at least a user-defined number of dark pixels and it is bounded above by a threshold number of light pixels on both sides, then the edge defined by the transition between light and dark pixels may be used as a landmark as long as those points along one or both edges continue for at least a length greater than another threshold. In another example, the detected edge is identified as a blood vessel if a linear regression of the pixels of the edge yields a straight line having an R-squared or other measure of fitness greater than a target threshold, such as 0.8 in an example.

The landmarks may have different morphologies in an endoscopic map. In an example, a landmark may be represented in the endoscopic image as a line segment. In another example, the landmarks may be represented in the endoscopic image as two or more line segments intersecting at a point, which is referred to as an intersecting landmark, or a point landmark. In some examples, for two non-intersecting and non-parallel line segments close to each other (such as within a specific distance range), the landmark detector 321 may algorithmically extend one line segment until it intersects with the other line segment to create a point landmark.

The landmark detector 321 may localize the landmarks relative to the aiming beam footprint in a coordinate system of the endoscopic image. For example, the location of a point landmark in an endoscopic map may be represented by a vector between the point landmark and the aiming beam footprint, or distances along the X and Y axes in the coordinate system. In some examples, the landmark detector 321 may determine inter-landmark spatial relations, such as distance and slope between the landmarks, in the coordinate system of the endoscopic image. Information about the landmarks and their locations, the aiming beam footprint, and inter-landmark spatial relations may be stored in the memory 340, and used for endoscopic image registration, target map reconstruction, or endoscopic tracking during an endoscopic procedure, according to various examples discussed in this document.

The landmark detector 321 may select a subset of the detected landmarks for storage in the memory 340, or for applications such as image registration, target map reconstruction, or endoscopic tracking. In an example, a subset of landmarks may be selected based on the landmark locations, such as a spatial distribution of the landmarks in the endoscopic image. For example, landmarks that are spread across the endoscopic image may be favorably selected over a cluster of closely-spaced landmarks in the endoscopic image. In another example, a subset of landmarks may be selected based on whether laser energy is activated at the target sites where the landmarks are located. Because laser energy may impact the landmark detection accuracy and consistency, in an example, a landmark that is not activated by laser energy may be more favorably selected over another landmark activated by laser energy.

In some examples, the endoscope controller 103 may control the light source 104 or the illumination lens 122 to produce special lighting conditions for the target 101 to improve landmark detection and localization. For example, the light source 104 may provide blue or green lighting to increase contrast on the endoscopic image of the target 101, and to more clearly define vasculature which is less likely to move or change over time. This allows for more consistent landmark detection and localization under slightly different illumination conditions. In an example, the endoscope controller 103 may temporarily alter the lighting, such as switching on green or blue light source for optimally identifying landmarks, and resume to normal illumination mode after the landmarks are identified.

The video processor 320 may include a target identifier 322 configured to identify a target type at the aiming beam location of the target 101. In an example, identification of target type may be based on one or more spectroscopic properties of an illuminating light reflected from the target 101. The spectroscopic properties may be measured using the spectrometer 208. The identified target type may include an anatomical tissue type or a calculus type. Examples of calculus type may include stones or stone fragments in various stone-forming regions such as urinary system, gallbladder, nasal passages, gastrointestinal tract, stomach, or tonsils. Examples of the anatomical tissue type may include soft tissue (e.g., muscles, tendons, ligaments, blood vessels, fascia, skin, fat, and fibrous tissues), hard tissue such as bone, connective tissue such as cartilage, among others. In an example, the target identifier 323 may identify the tissue type at the aiming beam location of the target 101 as normal and abnormal tissue, or mucosa or muscle tissue based on properties of the reflected illuminating signal.

The video processor 320 may mark the aiming beam footprint in the endoscopic image, as displayed on the display 108, with a visual identifier indicating the identified tissue type. In an example, the visual identifier can include a color code, such that the aiming beam footprint may be tinted with different colors to indicate different tissue types. For example, the aiming beam footprint may be tinted green if the target site is recognized as normal tissue, or tinted red if the target site is recognized as abnormal tissue (e.g., cancerous). In an example, the video processor 320 may mark the aiming beam footprint with a visual identifier indicating a change in tissue type over time (e.g., from normal to abnormal, or vice versa) at the target site, such as by using a different color than that representing normal or abnormal tissue. In another example, the video processor 320 may mark the aiming beam footprint with a visual identifier indicating a treatment status at the target site. For example, if the target site has been treated (e.g., with laser therapy) then the aiming beam footprint may be represented by a dot with a different color than that representing normal or abnormal tissue.

FIGS. 4A-4F illustrate by way of example and not limitation a sequence of endoscopic images (e.g., video frames) $\{G_1, G_2, \ldots, G_N\}$ taken at the target 101, such as an inside of a kidney, a bladder, a urethra, or a ureter, among other anatomies of interest. The endoscopic images may be displayed on the display 108. As discussed above, the endoscopic images may be taken at a same target site at different times, or at different target sites $\{S_1, S_2, \ldots S_N\}$ when the endoscope tip pans across the target 101. The target identifier 322 may identify target types at the aiming beam locations corresponding to the target sites $\{S_1, S_2, \ldots S_N\}$. The video processor 320 may mark the aiming beam footprints in the corresponding endoscopic images with respective visual identifiers (e.g., colors) identifying the corresponding target types, detect and localize landmarks from the endoscopic images, and integrate the endoscopic images into a target map of the target 101 based on the landmarks identified from the endoscopic images.

Figure 4A:
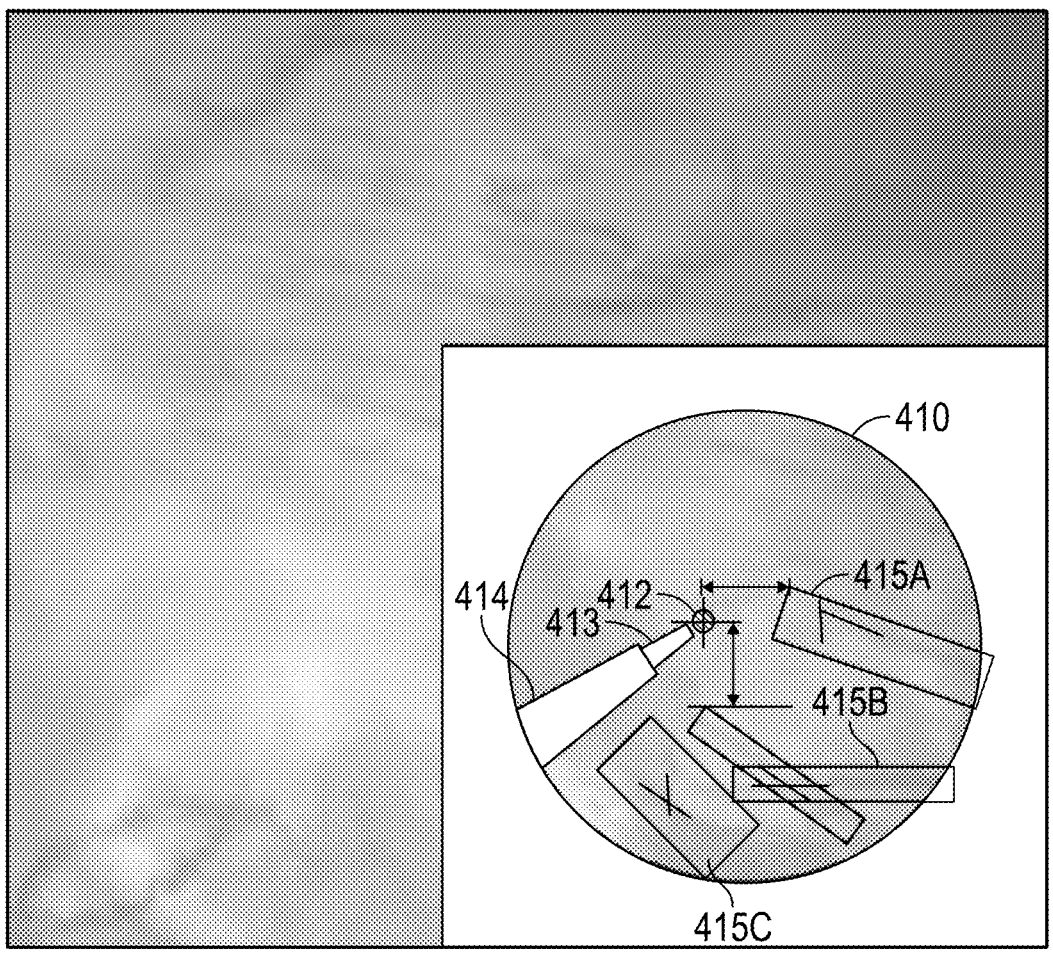
FIGS. 4A-4F illustrate examples of a sequence of endoscopic images or video frames captured at different target sites and landmarks and an aiming beam footprint detected therefrom.

Endoscopic images 410-460 as shown in FIGS. 4A-4F are generated as the endoscope tip pans across the target 101, during which the endoscope distal tip is moved and positioned, manually or automatically, at different endoscopic locations. FIG. 4A illustrates an endoscopic image 410 including a graphical representation of the illuminated target site $S_1$ that falls within the FOV of the imaging system 115, and a circular-shaped aiming beam footprint 412. The aiming beam footprint 412 is tinted green to indicate that the tissue at the aiming beam location is normal tissue. In this example, an image 413 of the distal tip 112a of the optical pathway 112 (e.g., a laser fiber) and an image 414 of a distal portion of the endoscope 102 are also shown in the image 410.

The image 410 also includes landmarks 415A-415C, such as detected by the target identifier 322. In this example, landmarks 415B and 415C are each represented by two line segments that intersect to form a point landmark, and landmark 415A is represented by two line segments algorithmically intersected (e.g., by projecting one line segment towards the other) to form a point landmark. Locations of the landmarks 415A-415C may be determined by the target identifier 322, as discussed above with reference to FIG. 3. The image 410, including information about the aiming beam footprint 412 and the landmarks 415A-415C, may be stored in the memory 340.

Figure 4B:
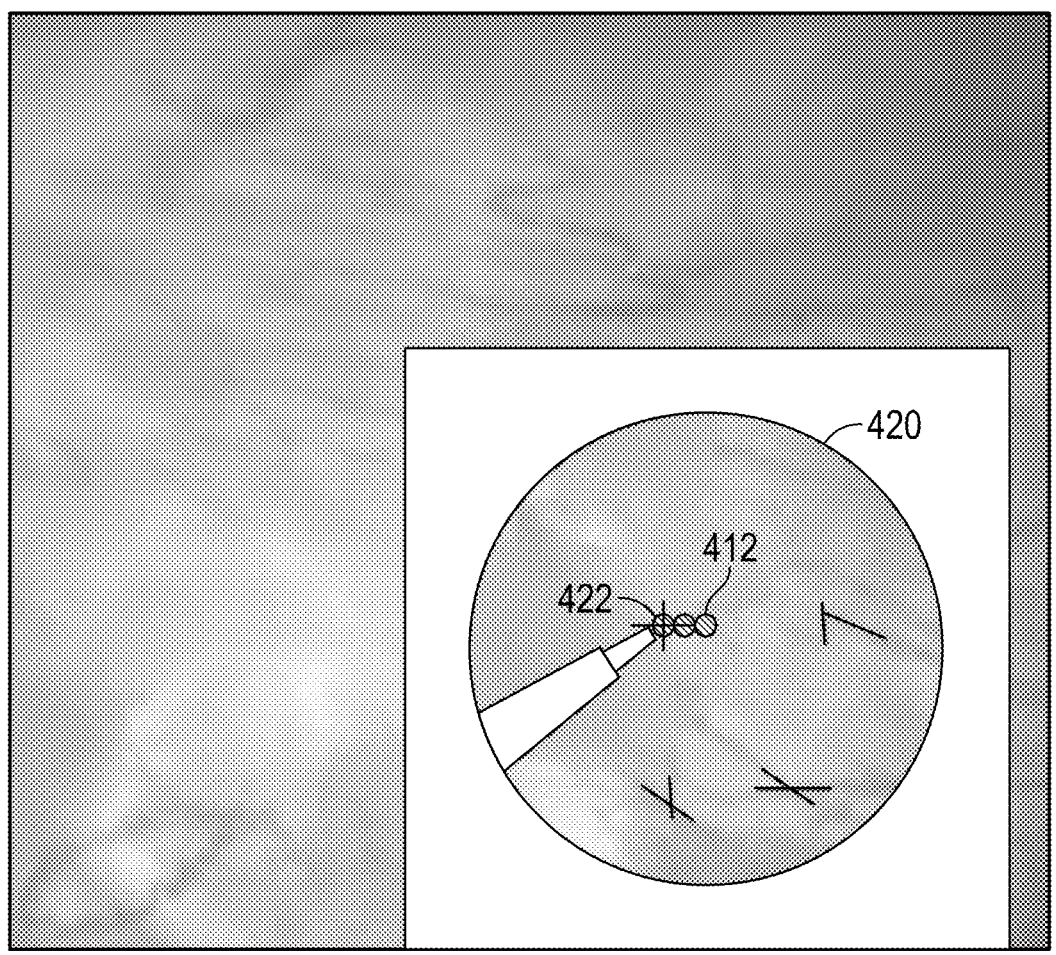

As the endoscope distal tip is moved, manually or automatically, to a new endoscopic location, another endoscopic image 420 as shown in FIG. 4B may be generated. The new endoscopic image 420 includes a graphical representation of the new illuminated target site $S_2$ corresponding to the new endoscopic location, and a new aiming beam footprint 422. As the tissue at the present aiming beam is recognized as normal tissue, the aiming beam footprint 422 is tinted green. New landmarks, if detected from the present endoscopic image, may be included in the image. In this example, no new landmark is detected from the endoscopic image 420. Previous aiming beam footprint 412 and previously generated landmarks 415A-415C, if located within FOV of the imaging system at the current endoscope location, may be kept in the present image 420.

If the movement of the distal tip is made with a small step size, the illuminated target sites $S_1$ and $S_2$ may overlap, such that the two endoscopic images 410 and 420 may both cover a common region of the target 101, as illustrated in FIGS. 4A and 4B. One or more matching landmarks may be identified from the endoscopic images 410 and 420. Such matching landmarks may be used to align the images 410 and 420 to reconstruct a map of the target, according to various examples to be discussed in the following.

Figure 4C:
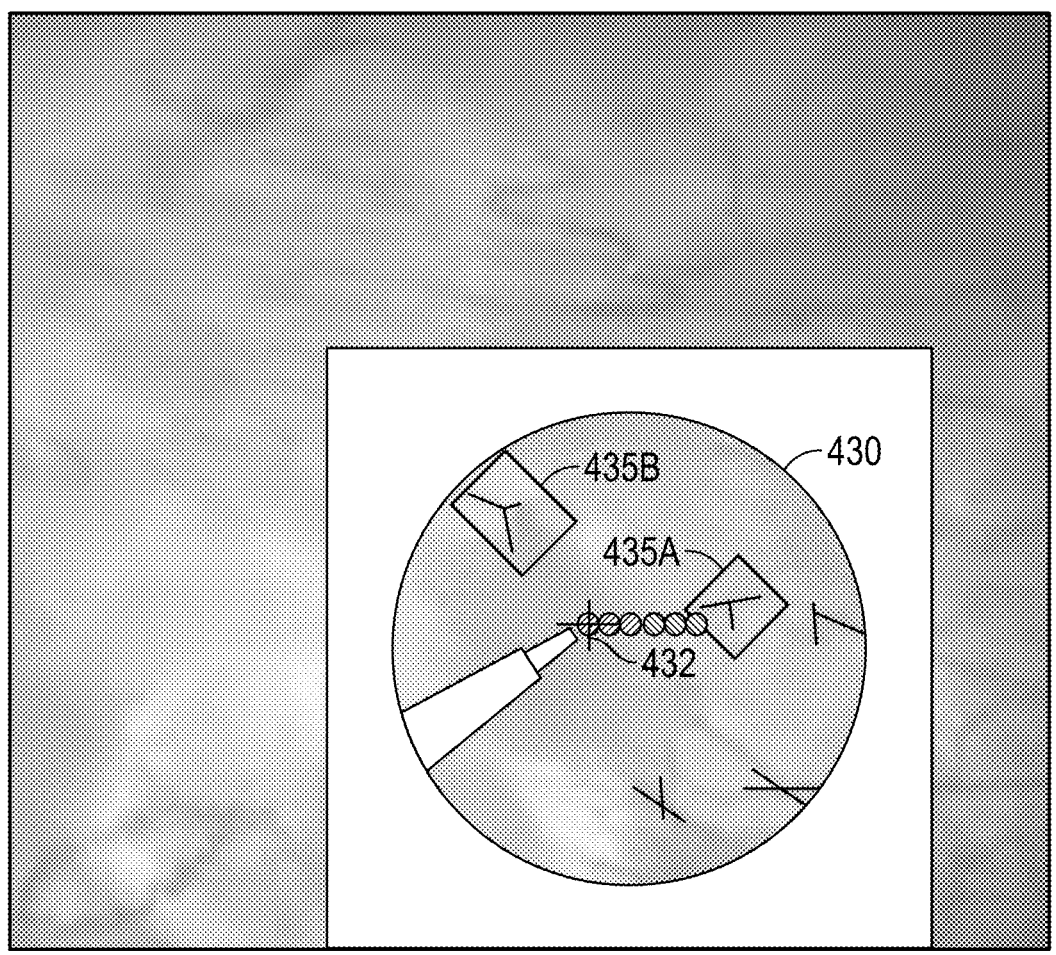

The endoscope panning process may be continued, and additional endoscopic images may be generated. FIG. 4C shows an image 430 including a graphical representation of the new illuminated target site $S_3$, and a new aiming beam footprint 432 tinted red indicating abnormal tissue is recognized at the present aiming beam location. New landmarks 435A-435B may be detected from the present endoscopic image. Previous aiming beam footprints and previously generated landmarks (e.g., 415A-415C) are still within the FOV of the imaging system at the current endoscope location, and may be kept in the image 430.

Figure 4D:
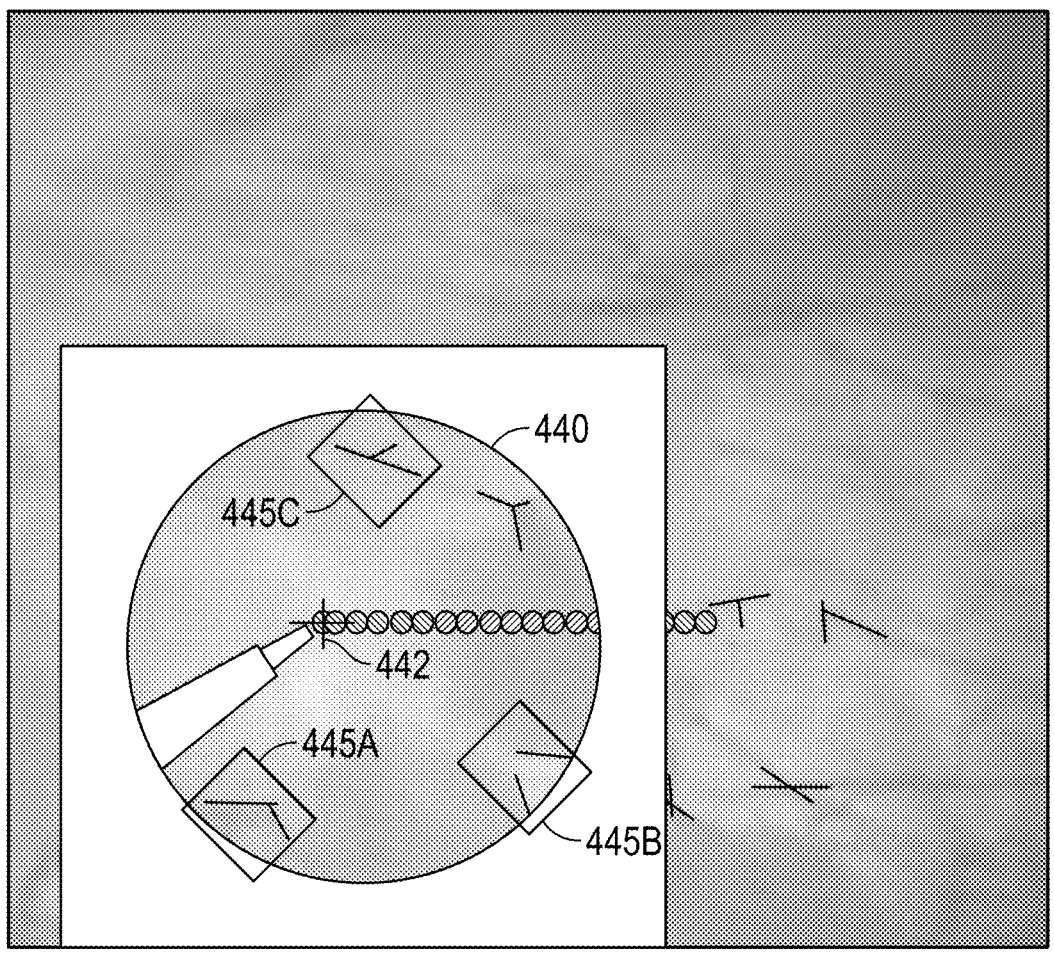

FIG. 4D shows an image 440 including a graphical representation of the new illuminated target site $S_4$, and a new aiming beam footprint 442 tinted green indicating normal tissue is recognized at the present aiming beam location. New landmarks 445A-445C may be detected from the present endoscopic image. The new aiming beam footprint (including its location and color representing the tissue type) and the new landmarks (including their locations relative to the aiming beam footprint), and previous aiming beam footprints and previously generated landmarks, may be stored in the memory 340. Previous aiming beam footprints and previously generated landmarks (e.g., 435B) falling within the FOV of the imaging system at the current endoscope location may be kept in the image 440.

Figure 4E:
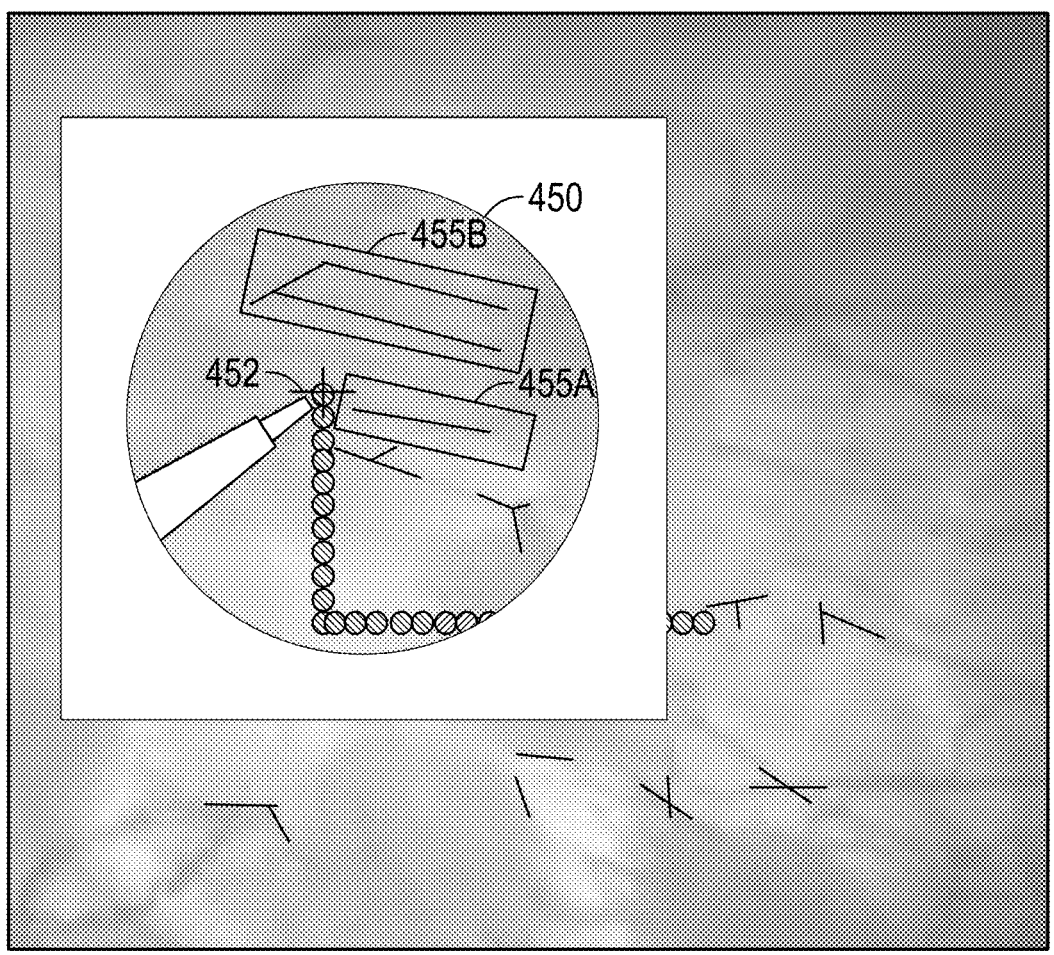

The endoscope distal tip may be moved, manually or automatically, along a specific path or following a specific pattern, such that the endoscopic images generated during the panning process may jointly provide a panoramic coverage of a substantial surface area of the target 101. As an non-limiting example, FIGS. 4A-4F illustrate a rectangular path, indicated by the aiming beam footprints in the corresponding endoscopic images. After leftward horizontal movements (as illustrated in FIGS. 4A-4D), the endoscope distal tip moves upward vertically, during which endoscopic images may be taken at respective target sites. FIG. 4E illustrates an image 450 including a graphical representation of the new illuminated target site $S_5$, and a new aiming beam footprint 452 tinted green indicating normal tissue is recognized at the present aiming beam location. New landmarks 455A-455B may be detected from the present endoscopic image. Previous aiming beam footprints and previously generated landmarks falling within the FOV of the imaging system at the current endoscope location are kept in the image 450.

Figure 4F:
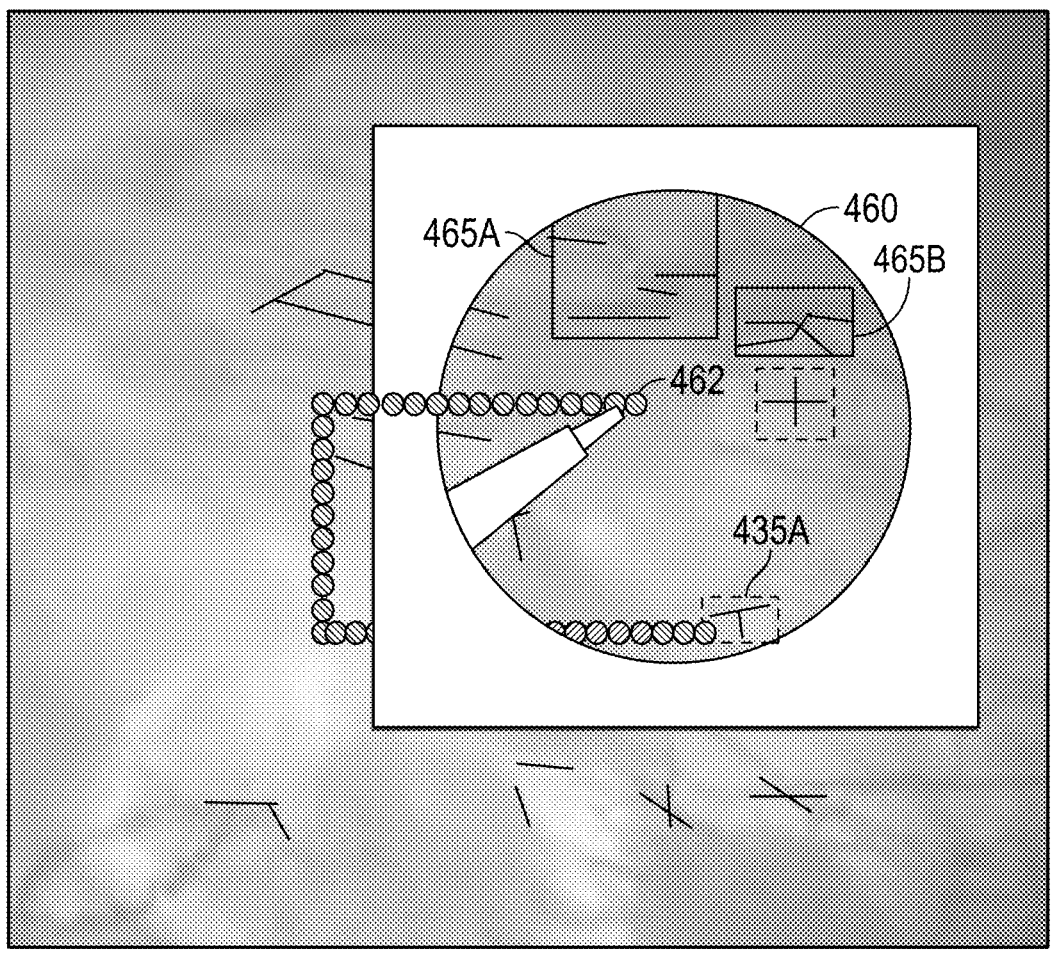

After the upward vertical movement, the endoscope distal tip takes rightward horizontal movement, during which endoscopic images may be taken at respective target sites. FIG. 4F shows an image 460 including a graphical representation of an illuminated target site $S_6$, which includes a portion of previously visited illuminated site captured in image 410, and a new aiming beam footprint 462 tinted green indicating normal tissue is recognized at the present aiming beam location. New landmarks 465A-465B may be detected from the present endoscopic image. Previous aiming beam footprints and previously generated landmarks falling within the FOV of the imaging system at the current endoscope location are kept in the image 460. This includes the previously generated landmark 435A, which once fell outside of endoscopic images 440 and 450.

Returning to FIG. 3, the video processor 320 can include a target map generator 323 configured to reconstruct a target map by integrating a plurality of endoscopic images (or video frames) {$G_1, G_2, \ldots, G_N$} of various target sites of the target 101 stored in the memory 340. As discussed above with reference to FIGS. 4A-4F, the stored endoscopic image $G_i$ may include a graphical representation of an illuminated target site, an aiming beam footprint (including its location and color representing the tissue type), and one or more landmarks (including their locations relative to the aiming beam footprint and inter-landmark spatial relations). The target map generator 323 may perform image registration to align the stored endoscopic images {$G_1, G_2, \ldots, G_N$} based on the landmarks with relative locations. The image registration may include identifying matching landmarks, including two or more landmarks identified from a first endoscopic image (e.g., image $G_i$ taken at a first target site $S_i$) that match two or more landmarks identified from a second endoscopic image (e.g., image $G_j$ taken at a different second target site $S_j$), and align the second image to the first image with respect to the identified matching landmarks. For example, the image 430 of FIG. 4C may be aligned with the image 420 of FIG. 4B using matching landmarks 415A-415C that are present in both images 420 and 430. The aligned images may then be stitched together with respect to the matching landmarks to reconstruct a target map. In some example, the landmark detector 321 may adjust the landmark detection algorithm (e.g., reducing a threshold value for edge detection) to allow more landmarks to be identified from an endoscopic image. Multiple landmarks may increase the probability of identifying matching landmarks between images, and improve image alignment accuracy.

Figure 5:
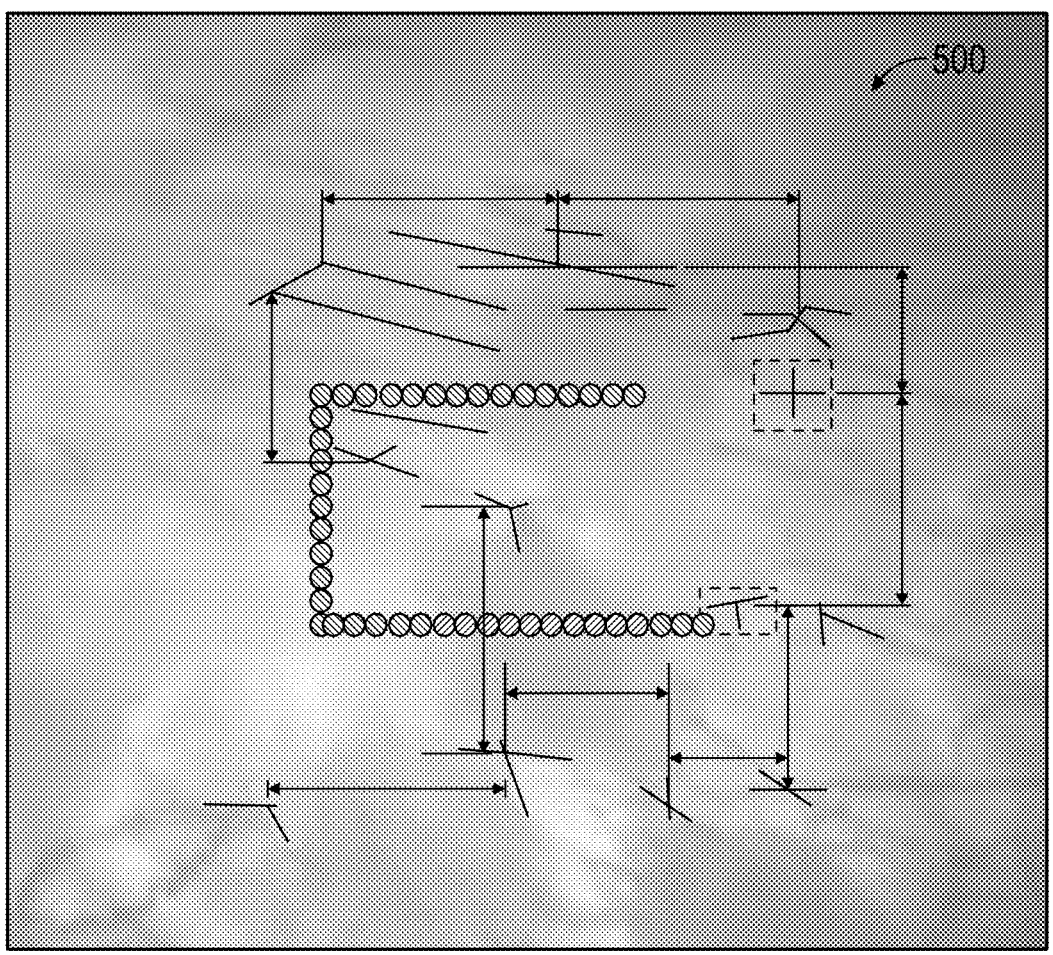
FIG. 5 illustrates an example of a target map reconstructed from multiple endoscopic images or video frames captured at different target sites.

FIG. 5 illustrates an example of a target map 500 of the target 101, such as a substantial region of a bladder. In additional to the stitched images, the reconstructed map may additionally include one or more of a set of landmarks identified from the plurality of endoscopic images, aiming beam footprints, target type identifiers (e.g., color codes for the aiming beam footprints), landmark locations relative to the aiming beam footprints, or inter-landmark spatial relations. The target map 500 may be used to assist in medical diagnosis or therapy planning, such as to localize and track endoscope location during an endoscopic procedure.

Geometric distortions or deformations may be introduced to the endoscopic images used for reconstructing a target map (e.g., endoscopic images 410-460 in FIGS. 4A-4F used for reconstructing the target map 500 in FIG. 5), resulting in mismatches of common regions between images. For example, moving the endoscope distal tip closer to or farther away from the target, or body motion (e.g., breathing), may cause image magnification or shrinkage. A change in viewing direction (from the imaging system 115 at the endoscope distal tip towards the target) may cause image rotation. In some instances, geometric distortions or deformations may be caused by a change in endoscope orientation. In this document, endoscope orientation refers to a tilt or skew of the endoscope tip with respect to the target surface. A change in endoscope orientation from one image to another may cause distortions in length, shape, and other geometric properties. To correct for such distortions or deformations, in some examples, the target map generator 323 may transform an image before aligning it with another image. Examples of the image transformation may include one or more of scaling, translation, rotation, or a shear transformation of an image in a coordinate system, among other rigid, similarity-based, or affine transformations. In an example, an image may be scaled by a scaling factor based on inter-landmark distances measured respectively from the two images, or a scaling factor based on geometric features measured respectively from the aiming beam footprints in the two images, such as described in the following with respect to FIG. 7. In an example, a change in endoscope orientation may be corrected for based on slopes between landmarks respectively measured from the two images, or based on geometric features respectively measured from the aiming beam footprints in the two images, such as described in the following with respect to FIGS. 6A-6F.

The transformation may be implemented as a transformation matrix multiplied by image data (e.g., a data array). The transformed image may be aligned with another image with respect to the matching landmarks between the two images. In some examples, the alignment may be based on slopes of multiple landmarks relative to each other. Such an alignment may be insensitive to the distance between the landmarks (related to differences in magnification, or distance of the endoscope from the target). The image transformation according to various examples as described in this document can improve robustness of target map reconstruction to differences in endoscopic image rotation, magnification, or shrinkage.

Landmarks in the transformed endoscopic image many be saved in their transformed state in the memory 340 as if on a two-dimensional projected surface of the target. As such, the landmarks in the transformed endoscopic images are invariant to surface non-uniformities, skew, rotation, scale, among other distortions or deformations. The saved transformed endoscopic images may be integrated to form an integrated target map. The saved landmarks may serve as the basis for comparison for new images, or for transforming new images to two-dimensional projected surfaces and registering the new image to the saved target map such as described in the following with reference to FIG. 7.

FIGS. 6A-6F are diagrams illustrating effects of endoscopic orientation on endoscopic image properties and methods of correcting for different endoscopic orientations between two endoscopic images. The endoscopic orientation correction methods discussed herein may be applied to image registration applications such as registering a real-time intraoperative endoscopic image to a target map (such as the target map 500), as to be discussed in the following with reference to FIG. 7. An endoscopic orientation refers to a tilt or skew angle θ of the lens system 118 with respect to the target surface. For two endoscopic images $G_i$ and $G_j$ taken with different endoscopic orientations, image properties such as landmark locations (e.g., distance to the aiming beam footprint) and inter-landmark spatial relations (e.g., inter-landmark distances) are measured in respective coordinate systems of the two images. If $G_i$ and $G_j$ are endoscopic images of the same target site, by correcting for such an endoscopic orientation difference, the image properties of the endoscopic images $G_i$ and $G_j$ are measured in the same coordinate system. Assessment of anatomical differences or similarities based on the image properties (e.g., inter-landmark distances) between the two images is more robust to different imaging conditions. If $G_i$ and $G_j$ are endoscopic images of different target sites (such as two of the images in FIGS. 4A-4F during endoscope panning), by correcting for such an endoscopic orientation difference, inconsistency between the endoscopic images $G_i$ and $G_j$ may be reduced, and an integration of $G_i$ and $G_j$ (as a part of the target map 500) may provide a more reliable representation of an extended surface area of the target 101

FIG. 6A illustrates a first endoscopic orientation θ1 where the tip of the endoscope 102 is perpendicular to a surface of the target site 611 (that is, θ1=90 degrees), and the lens system 118 is parallel to the target site 611. An endoscopic image 615 taken at the endoscopic orientation θ1 is shown in FIG. 6C. FIG. 6B illustrates a second endoscopic orientation θ2 where the tip of the endoscope 102 is titled against the target site 621 (that is, θ2 is an acute angle), and the lens system 118 is not parallel to the target site 621. An endoscopic image 625 taken at the endoscopic orientation θ2 is shown in FIG. 6D. Matching landmarks {$M_1, M_2, M_3$}, such as in a form of intersecting line segments, may be identified by the landmark detector 321 form the endoscopic images 615 and 625.

The target map generator 323 may detect a change in endoscopic orientation from θ1 to θ2 using features generated respectively from the images 615 and 625, transform the endoscopic image 625 to correct for the change in endoscopic orientation, and align the transformed image 625 with the image 615 with respect to the matching landmarks {$M_1, M_2, M_3$}. As illustrated in FIGS. 6C and 6D, due to the difference in endoscopic orientation, inter-landmark spatial relationships (e.g., distances and relative locations) among the landmarks {$M_1, M_2, M_3$} in image 615 may appear differently than relative locations among the landmarks {$M_1, M_2, M_3$} in image 625. In an example, the inter-landmark spatial relationship may be represented by a slope between two landmarks in a coordinate system, such as a slope $k_{13}$ between landmarks $M_1$ and $M_3$, which may be computed as a ratio of a distance in the y-axis between $M_1$ and $M_3$, $y_{13}$, to a distance in the x-axis between $M_1$ and $M_3$, $x_{13}$, that is, $k_{13}=y_{13}/x_{13}$. To determine the change in endoscopic orientation, the target map generator 323 may compare a first slope between two landmarks (e.g., $k_{13}=y_{13}/x_{13}$) in the image 615, and a second slope between the same two landmarks (e.g., $k_{13'}=y_{13'}/x_{13'}$) in the image 625. In the illustrated example, a relative slope, such as a ratio between $k_{13}$ and $k_{13}'$, may indicate the change in endoscopic orientation.

Additionally or alternatively, in some examples, the target map generator 323 may detect a change in endoscopic orientation using geometric features generated respectively from the aiming beam footprints in the images 615 and 625. FIGS. 6A and 6B illustrate the distal tip 112a of laser fiber (an example of the optical pathway 112) directing the aiming beam at the respective target site. The resulting aiming beam footprints 612 and 622, as illustrated in respective endoscopic images 615 and 625, have different geometric properties due to the difference in endoscopic orientation. Corresponding to the endoscopic orientation θ1=90°, FIG. 6E illustrates an circular-shaped aiming beam footprint 612 with a dimeter of d. Corresponding to the endoscopic orientation θ1<90°, FIG. 6F illustrates an elliptical-shaped aiming beam footprint 622 having a major axis 623 with a length "a" and a minor axis 624 with a length "b" In an example, the target map generator 323 may determine the endoscopic orientation using an ellipse axis length ratio $R_e=a/b$. For the elliptical-shaped footprint 622, the ellipse axis length ratio $R_e>1$. A larger ellipse axis length ratio indicates a more tilted endoscopic orientation. For the circular-shaped footprint 612 with a diameter d, the major and minor axes a=b=d, and the ellipse axis length ratio $R_e=1$. The target map generator 323 may determine the change in endoscopic orientation based on a comparison between the ellipse axis length ratio respectively calculated from the aiming beam footprints 612 and 622, transform the endoscopic image 625 to correct for the change in endoscopic orientation, and align the transformed image 625 with the image 615 with respect to the identified matching landmarks.

Referring back to FIG. 3, the endoscopic tracker 330 may localize and track endoscope tip during an endoscopic procedure using a pre-generated target map (e.g., target map 500 as shown in FIG. 5). The endoscopic tracking may begin with capturing a real-time image or video signal from a procedure site of the target 101 using the imaging system 115, and generating a real-time image or video frame using the video processor 320, as similarly discussed above with regard to generating an endoscopic image (e.g., one of those shown in FIGS. 4A-4F) for reconstructing the target map 500. The imaging system 115 may be positioned at an unknown endoscopic location. The landmark detector 321 can identify one or more landmarks from the real-time image. The endoscopic tracker 330 can register the real-time image to a pre-generated target map of the target 101 (e.g., the target map 500), and locate, from the target map, the site captured in the real-time image.

The endoscopic tracker 330 may determine a change in tissue status (e.g., a change from normal tissue to abnormal tissue, or vice versa) at the target site. The endoscopic tracker 330 may localize and track the endoscope tip during the procedure such as based on the landmarks identified from the real-time image and the stored landmarks associated with the target map. In an example, the endoscopic tracker 330 can recognize two or more matching landmarks between the landmarks of the target map and the landmarks of the real-time image, register the real-time image to the target map using the recognized matching landmarks, and localize and track the endoscope tip based on the registration of the real-time image.

Figure 7:
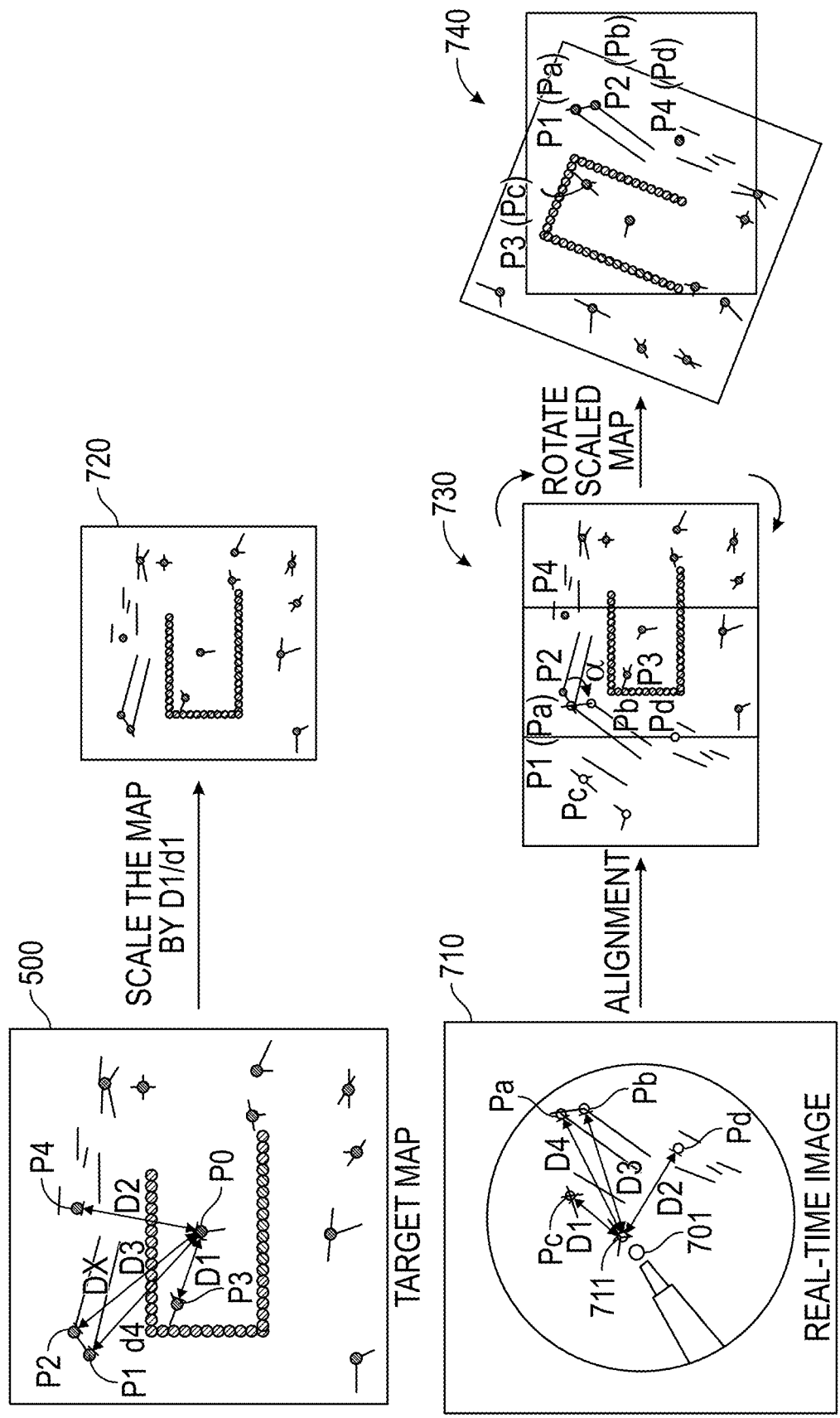
FIG. 7 illustrate an example of recognizing matching landmarks between a real-time image and a reconstructed target map, and registering the real-time image to the target map with respect to the matching landmarks.

FIG. 7 illustrate an example of recognizing matching landmarks between a real-time image 710 and a reconstructed target map 500, and registering the real-time image 710 to the target map 500 with respect to the matching landmarks. In an example, the matching landmarks may be recognized based on a distance ratio (r) between landmarks. As discussed above with reference to FIG. 5, the target map 500 contains pairwise inter-landmark distances {d1, d2, d3, . . . , $d_K$}, where K represents the number of landmark pairs identified from the target map 500. Distance ratios {r1, r2, . . . , $r_M$} may be computed between any two of the K inter-landmark distances {d1, d2, d3, . . . $d_K$}, where M represents the number of distance ratios.

According to one example, to recognize matching landmarks, the endoscopic tracker 330 may identify, among a set of intersecting landmarks (i.e., intersecting line segments) with respective intersecting point locations, an intersecting landmark 711 that is closest to the present aiming beam footprint 701 in the real-time image. Distances from the landmark 711 to other landmarks in the image 710 may be measured: D1 the distance to Pc, D2 the distance to Pd, D3 the distance to Pb, and D4 the distance to Pa, etc. The endoscopic tracker 330 can then calculate distances ratios (R) between the distances originating from the same landmark, such as the landmark 711 in this example: R1=D1/D2, R2=D1/D3, R3=D1/D4, etc. The distance ratios {R1, R2, R3} may be compared to the distance ratios {r1, r2, . . . , rM} associated with the target map 500. When the distance ratios {R1, R2, R3} (corresponding to the originating landmark 711 in the real-time image 710) match the distance ratios {rx, ry, rz} (corresponding to the originating landmark Pk in the target map 500) such that R1=rx, R2=ry, and R3=rz, then there is a high probability that the distances {D1, D2, D3, D4} match the distance {d1, d2, d3, d4}; and that the landmarks {Pa, Pb, Pc, Pd} in the real-time image 710 match the landmarks {p1, p2, p3, p4} in the target map 500. The more distances that may be matched, the higher the probability of matching landmarks between the real-time image 710 and the map 500.

The endoscopic tracker 330 may then determine a correspondence between the distances {D1, D2, D3, D4} and the distance {d1, d2, d3, d4} based on a ratio of distances between landmarks. For example, if D1/D2=d1/d2, then it may be determined that D1=d1, and D2=d2. By checking various combinations until they all match, the endoscopic tracker 330 may identify which distance in {D1, D2, D3, D4} corresponds to which distance in {d1, d2, d3, d4}. Since all matching was done relative to D1, with the identification of D1 as d1, the rest distances D2, D3, and D4 may be matched to d2, d3, and d4 accordingly. With the established correspondences between D1 and d1, between D2 and d2, between D3 and d3, and between D4 and d4, the correspondence between {Pa, Pb, Pc, Pd} and {p1, p2, p3, p4} may also be determined.

The endoscopic tracker 330 may register the real-time image 710 to the target map 500 using the identified matching landmarks {Pa, Pb, Pc, Pd} in the real-time image 710 that match the landmarks {P1, P2, P3, P4} in the target map 500. To correct for geometric distortions or deformation of images such as due to image magnification, shrinkage, rotation, or change in endoscopic orientation, the endoscopic tracker 330 may transform the real-time image 710 or the target map 500 in a similar fashion as discussed above with regard to transforming a first endoscopic image, aligning it with a second endoscopic image, and reconstructing a panoramic target map using at least the transformed first image and the second image, as discussed above with reference to FIGS. 4A-4F. The transformations may include one or more of scaling, translation, or rotation, among other operations. The transformation may be implemented as a transformation matrix multiplied by image data (e.g., a data array) of the target map 500 in a coordinate system of the real-time image 710. Alternatively, the transformation may be applied to the real-time image 710.

As illustrated in FIG. 7, the transformation may include scaling the map 500 by a scaling factor λ to correct for different image magnification or shrinkage between the real-time image 710 and the map 500. The scaled map 720 includes landmarks with their locations (e.g., relative distances to the aiming beam footprints) and inter-landmark distances also scaled by the scaling factor λ. In an example, the scaling factor λ may be determined using a ratio of a distance between two matching landmarks (e.g., P1 and P2) in the real-time image 710 to a distance between the corresponding two landmarks (e.g., Pa and Pb) in the map 500. In an example, the largest inter-landmark distance among the matching landmarks in the real-time image 710 may be selected for computing the distance ratio λ. For example, if D4 is the largest distance among {D1, D2, D3, D4}, then the scaling factor λ=D4/d4.

The scaling factor λ may alternatively or additionally be determined using a comparison between the shape of the aiming beam footprint in the real-time image 710 and the shape of the aiming beam footprint in the map 500. In an example, the scaling factor λ may be determined using a ratio of a geometric feature of the aiming beam footprint in the real-time image 710 to a corresponding geometric feature of the aiming beam footprint in the map 500. For example, if the real-time image 710 has a circular-shaped footprint (as illustrated in FIG. 6E) with a diameter $d_R$ and the map 500 has a circular-shaped footprint with a diameter $d_M$, then the scaling factor $\lambda = d_R/d_M$. In an example, if the real-time image 710 has an elliptical-shaped footprint (as illustrated in FIG. 6F) with a major axis length of $a_R$ and a minor axis length of $b_R$, and the map 500 has an elliptical-shaped footprint with a major axis length of $a_M$ and a minor axis length of $b_M$, then the scaling factor $\lambda = a_R/a_M$, or $\lambda = b_R/b_M$.

The scaling factor λ computed as above assumes that the surface onto which the aiming beam is projected is a flat surface. In some instances, the aiming beam projection surface may not be perfectly flat, but instead have a three-dimensional shape. This may introduce variation in the calculated scaling factor λ. The system may accommodate variations from an ideal scaling factor λ. In an example, multiple aiming beam footprints may be captured when the aming beam is direted at slightly different locations of the target site with respective projection surfaces. An overlay of the multiple aiming beam footprints may reveal the variation in the shape of the aiming beam footprints. Geometric features (e.g., diameter of a circular-shaped footprint or major or minor axis length of an elliptical-shaped footprint) may be measured respectively from the multiple aiming beam footprints, and corresponding multiple scaling factors be calculated. An average or weighted average of the multiple scaling factors may be carried out to obtain an expected value of the scaling factor λ.

Determination of the scaling factor λ as discussed above is based on an assumption of substantially no change in endoscopic orientation between the real-time image 710 and the map 500 (e.g., substantially identical tilt of skew of the endoscopic tip with respect to the target surface). In the presence of substantially different endoscopic orientations, metrics such as landmark locations, inter-landmark distances, shapes of aiming beam footprints and their geometric properties (e.g., lengths of major and minor axes) may be affected by the endoscopic orientation. The real-time image 710 or the map 500 may be transformed to correct for the change in endoscopic orientation, such as in accordance with the descriptions with respect to FIGS. 6A-6F. Scaling factor λ may then be determined from the transformed images.

The scaled map 720 (including the landmarks therein) may be aligned to the target map 500 with respect to the identified matching landmarks, such as P1 and Pa, as shown in diagram 730. The real-time image 710 may be translated towards the scaled map 720 such that Pa is at the same coordinate as P1 of scaled map 720, denoted by P1(Pa). The scaled map 720 can then be rotated 730 clockwise with an angle α, or ∠ Pb–P1(Pa)–P2. After the rotation, the matching landmark Pb is at the same coordinate as P2 of scaled map 720, denoted by P2(Pb), as illustrated in a registered map 740. Because the scaling and rotation operations preserve the relative locations (e.g., angles) between landmark, other matching landmarks P3 and P4 also overlap with landmarks Pc and Pd on the scaled map 720, denoted by P3(Pc) and P4(Pd) in the registered map 740. The real-time image 710 is thus registered to the target map 500, with respect to the matching landmarks P1-P4 (corresponding to Pa-Pd in the image 710).

The registration of a real-time image taken during an endoscopic procedure to the target map as discussed above may be used in a variety applications to improve endoscopic procedure precision and efficiency. In an example, the image registration may assist an operator in real-time identification of a procedure site from a pre-generated target map with improved accuracy. Because the target map stores information of endoscopic tip locations relative to a plurality of stored landmarks, the image registration as discussed herein may assist in localizing and tracking the endoscopic tip in real time throughout the procedure. For the target map that stores information about target type (e.g., normal or abnormal tissue) at various aiming beam locations of the target, the endoscopic tracker 330 may detect and track changes in tissue type over time at various target sites, or provide an assessment of effectiveness of a therapy delivered at the target.

Figure 8:
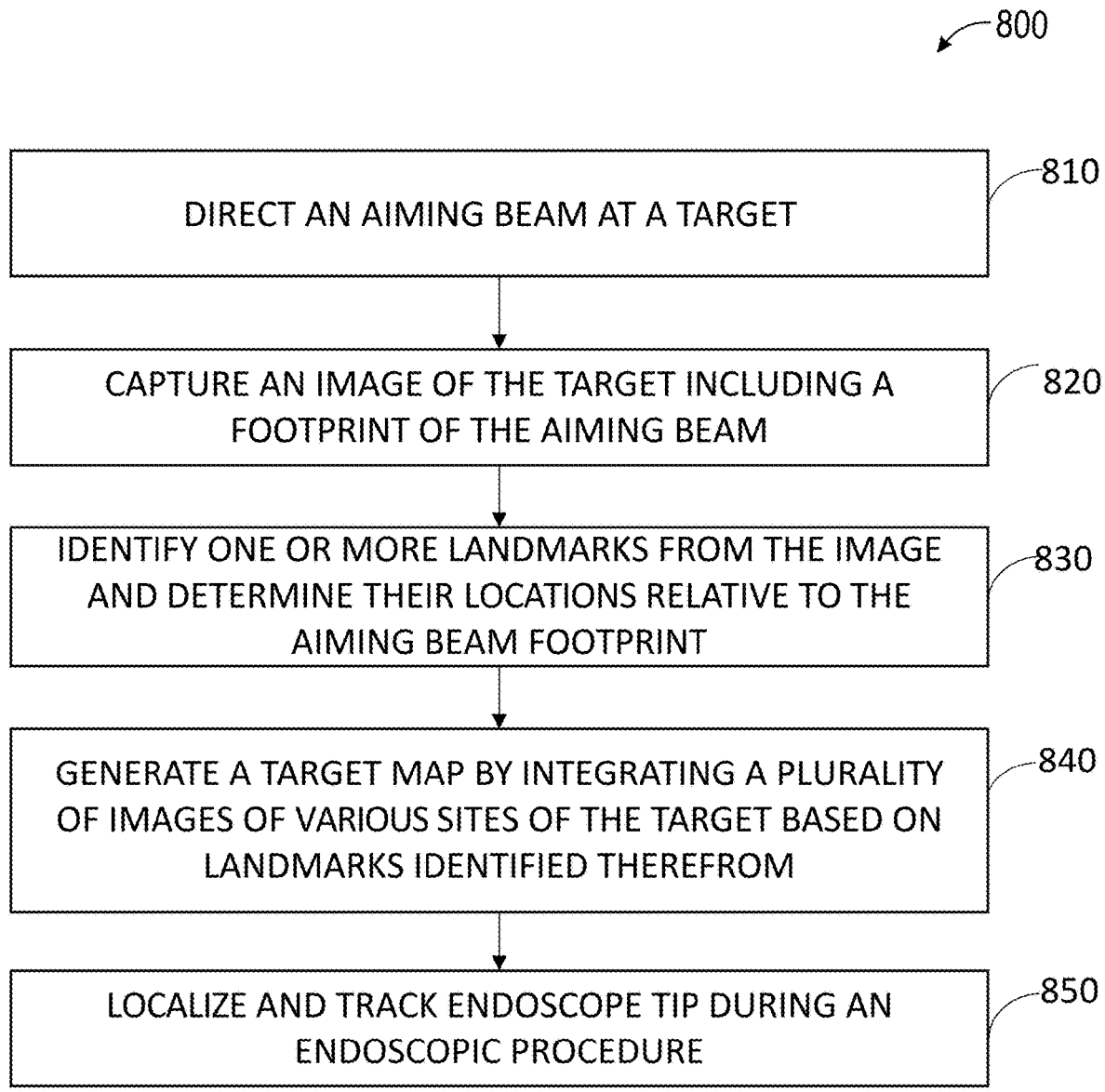
FIG. 8 is a flow diagram illustrating a method for endoscopic mapping of a target inside a subject body during a procedure.

FIG. 8 is a flow diagram illustrating a method 800 for endoscopic mapping of a target inside a subject body during a procedure. The method 800 may be implemented in and executed by a medical system for use in an endoscopic procedure, such as the system 100 or a variant thereof. Although the processes of the method 800 are drawn in one flow chart, they are not required to be performed in a particular order. In various examples, some of the processes may be performed in a different order than that illustrated herein.

At 810, an aiming beam may be emitted from an endoscope tip and directed at a site of the target, such as a portion of the target 101. The aiming beam may be produced by a laser source, such as the second laser energy source 204. Alternatively, the aiming beam may be produced by other light sources and transmitted such as via an optical fiber.

At 820, an image of the target site may be captured by an imaging system, such as the imaging system 115. The image may be taken when the lens system 118 of the imaging system 115 is positioned at an endoscopic location. The image may be taken when the target is illuminated with electromagnetic radiation (also referred to as illumination light) within an optical range from UV to IR. The illumination light may be produced by a light source, such as the light source 104, and transmitted to the target site via a light guide 120. In an example, the light source 104 may include two or more light sources that emit light having different illumination characteristics.

The aiming beam directed at the target site may fall within the FOV of the imaging system, such that the image captured at the target site may include not only a graphical representation of the illuminated target (e.g., a surface of target anatomy), but a footprint of the aiming beam as well. The image may be displayed to a user such as on a display 108, as illustrated in any of FIGS. 4A-4F. The aiming beam footprint may be tinted with a color different from the background of the endoscopic image. In an example, the location of the aiming beam footprint may be identified from the endoscopic image by matching the color of the aiming beam to the color of pixels in the endoscopic image.

The signal reflected from the target in response to an illuminating light may be analyzed, such as using the spectrometer 208, to identify a target type at the aiming beam location of the target. In an example, based on spectroscopic properties of the reflected signal, tissue at the target site may be identified as normal and abnormal tissue, or mucosa or muscle tissue, among other anatomical structure types. In some examples, the target site may be identified as one of one of a plurality of calculus types with respective compositions.

The aiming beam footprint in the endoscopic image may be marked with a visual identifier indicating the tissue type at the aiming beam location of the target. In an example, the aiming beam footprint may be tinted with different colors to indicate different tissue types. For example, the aiming beam footprint may be tinted green if the target site is recognized as normal tissue, or tinted red if the target site is recognized as abnormal tissue (e.g., cancerous). In some examples, the aiming beam footprint may be marked with an identifier to indicate a change in tissue type over time, or to indicate a treatment status.

At 830, one or more landmarks may be identified from the captured image of the target site, and the landmark locations relative to the aiming beam footprint may be determined, such as using the video processor 320. In an example, a landmark represents an anatomical structure (e.g., a blood vessel). The landmark may be detected based on variation in brightness of pixels of the endoscopic image. In an example, the landmarks may be detected using edge detection constrained by a contrast threshold, and number of pixels between similar positive and negative contrast slopes.

Locations of the one or more landmarks, such as X and Y distances in a coordinate system of the endoscopic image, may be determined relative to the aiming beam footprint in the same endoscopic image. In another example, the landmark localization involves determining inter-landmark landmark distances in the coordinate system of the endoscopic image. In some examples, a subset of the detected landmarks may be selected based on a spatial distribution of the landmarks in the endoscopic image. For example, the selected subset may include landmarks distributed across the endoscopic image (as opposed to a cluster of closely-spaced landmarks at one region of the image). In another example, landmarks may be selected based on if the laser energy is activated over the landmarks, as the laser energy may distort such landmarks. For example, a landmark that is not activated by the laser energy may be more favorably selected over another landmark activated by the laser energy.

In some examples, the target may be illuminated by special lighting conditions to improve landmark detection and localization. For example, the target may be illuminated by blue or green lighting to increase contrast on the endoscopic image of the target, and to more clearly define vasculature which is less likely to move or change over time. This allows for more consistent landmark detection and localization under slightly different illumination conditions.

At 840, a target map may be reconstructed such as by integrating a plurality of images of various sites of the target based on respective landmarks identified from the plurality of images. For example, as the endoscope tip pans across the target either manually by an operator or automatically by an endoscope actuator, the endoscope distal tip is moved and positioned at different endoscopic locations $\{L_1, L_2, \ldots, L_N\}$, and the imaging system can capture a sequence of endoscopic images $\{G_1, G_2, \ldots, G_N\}$ at respective plurality of target sites $\{S_1, S_2, \ldots, S_N\}$ of the target that fall within the FOV of imaging system at respective endoscopic locations. Examples of a sequence of images (or video frames) captured at different sites of the target is shown in FIG. 4A-4F.

A target map may be reconstructed by integrating the plurality of endoscopic images $\{G_1, G_2, \ldots, G_N\}$. The endoscopic images $\{G_1, G_2, \ldots, G\ N\}$ may be aligned with respect to the landmarks identified from the images. In an example, between two endoscopic images $G_i$ and $G_j$, matching landmarks may be identified, including two or more landmarks identified from the image $G_i$ that match two or more landmarks identified from the image $G_j$. The images $G_i$ and $G_j$ can then be aligned with respect to the identified matching landmarks.

In some examples, an endoscopic image (e.g., $G_i$) may be transformed before being aligned with another endoscopic image (e.g., $G_j$). The transformation may correct for geometric image distortions or deformations, such as image magnification or shrinkage caused by the endoscope distal tip being moved closer to or farther away from the target or body motion (e.g., breathing), image rotation caused by a change in viewing direction towards the target from the imaging system, or distortions in length, shape, and other image properties caused by a change in endoscope orientation. Examples of image transformation may include one or more of scaling, translation, rotation, or a shear transformation of an image in a coordinate system, among other rigid, similarity-based, or affine transformations.

In an example, before aligning a first endoscopic image $G_i$ and a second endoscopic image $G_j$, the image $G_j$ may be scaled by a scaling factor $\lambda$ based on a ratio of a distance between two of the matching landmarks in the image $G_i$ to a distance between the corresponding two landmarks in the image $G_j$. In another example, the scaling factor $\lambda$ may be determined based on a ratio of a geometric feature generated from an aiming beam footprint in the image $G_i$ to a geometric feature generated from an aiming beam footprint in the image $G_j$. Examples of the geometric feature may include a diameter of a circular-shaped footprint, or major (or minor) axis length of an elliptical-shaped footprint, as discussed above with reference to FIG. 7.

In an example, before aligning a first endoscopic image $G_i$ with a second endoscopic image $G_j$ a changes in endoscopic orientation between the images $G_i$ and $G_j$ may be detected and corrected for. In an example, the change in endoscopic orientation may be determined based on a comparison between a first slope between two of the matching landmarks in the image $G_i$ and a second slope between the two matching landmarks in the image $G_j$. In another example, the change in endoscopic orientation may be determined based on a comparison between a first geometric feature of an aiming beam footprint in the image $G_i$ and a second geometric feature of an aiming beam footprint in the image $G_j$. In an example, at least one of the first or second aiming beam footprint has an elliptical shape with a major axis and a minor axis, and at least one of the first or the second geometric feature may include a ratio of the major axis length to the minor axis length of the elliptical-shaped aiming beam footprint, as discussed above with reference to FIGS. 6A-6F.

The transformed images may be aligned and integrated into a reconstructed target map, such as that shown in FIG. 5. The reconstructed map may include one or more of a set of landmarks identified from the plurality of endoscopic images, aiming beam footprints produced during the tissue painting process, target type identifiers (such as color-coded aiming beam footprints), locations of the landmarks with respect to the aiming beam footprints, or relative locations between landmarks. The target map, including information about the landmarks and aiming beam footprints, may be stored in the memory 340. At 850, the target map may be used to localize and track endoscope tip during an endoscopic procedure, as described below with reference to FIG. 9. Additionally or alternatively, the target map may be used to determine a change in tissue status (e.g., change from normal to abnormal, or vice versa) at a target site.

The systems and methods of image reconstruction and endoscopic tracking according to various examples discussed in this document can accommodate a tolerance around their measurements. Comparisons or equations described or inferred from the description herein are not limited to perfect equality. In an example, the systems and methods described herein can first compare values for perfect equality, but then gradually expand tolerances around each calculation to identify overlaps that are then treated as equal. For example, the algorithm can gradually expand the tolerance window from the ideal to a limit when comparing the anatomical map of the same patient from two different times that may differ by weeks, months, or years, or it can create a larger area around each landmark that is then checked for overlapping using standard statistical methods, such as a t-test or a Mann-Whitney comparison of Medians with a targeted confidence of 5 to 25% for example. In an example, the tolerance window or confidence interval may range between 0% to X % of the distance between each pair of landmarks being compared, where X % may be 20% in an example, or 25% in another example. Alternatively, the tolerance window or confidence interval may gradually increase until appropriate matches can be obtained between a significant majority of landmarks, such as approximately 70-100% of the landmarks are found to be matched.

Figure 9:
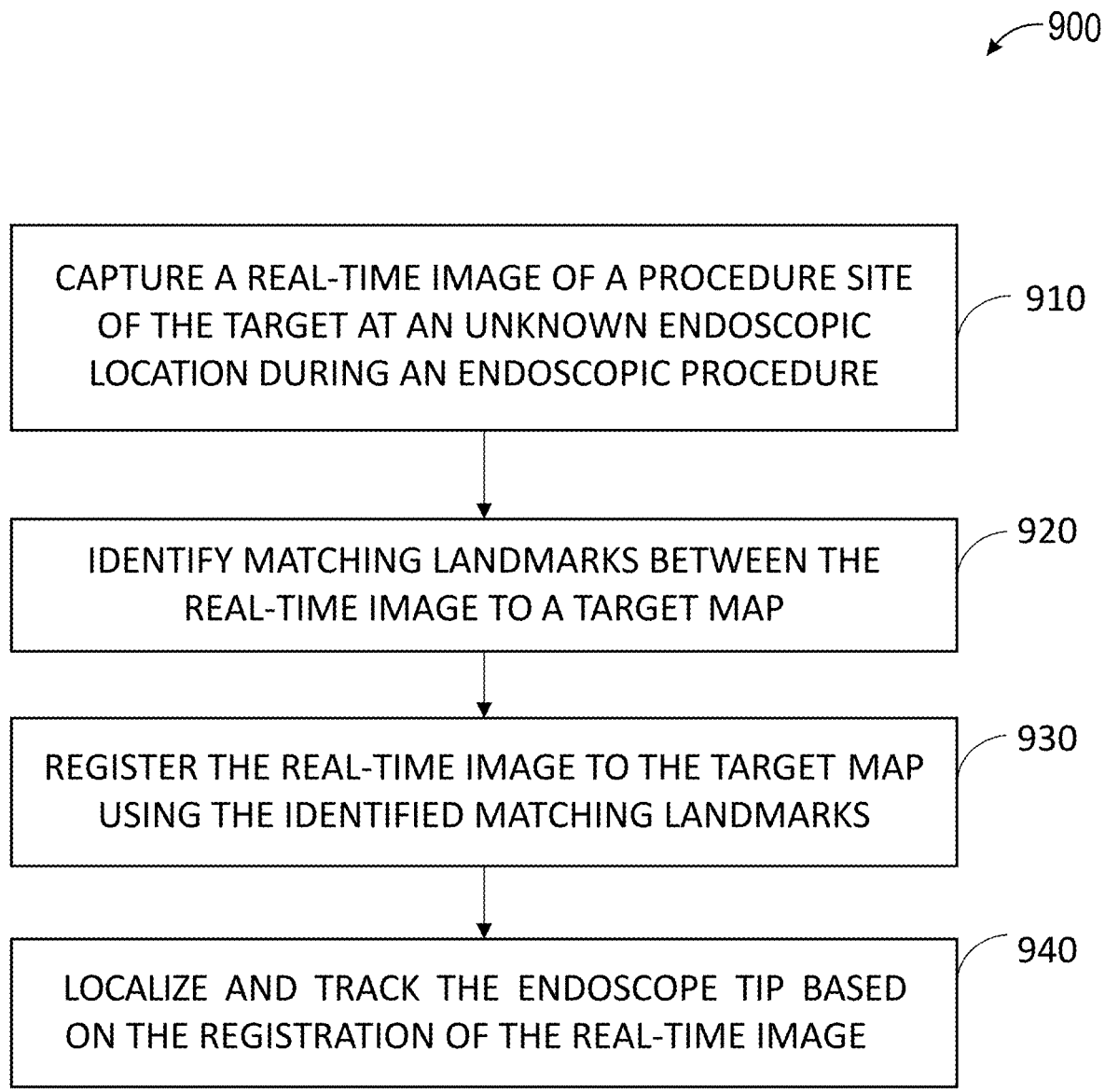
FIG. 9 is a flow diagram illustrating an example of a method for endoscopic tracking using a reconstructed target map.

FIG. 9 is a flow diagram illustrating an example of a method 900 for endoscopic tracking using a reconstructed target map, such as one generated using the method 800. At 910, during an endoscopic procedure a real-time image of a procedure site of the target site may be captured, such as via the imaging system positioned at an unknown endoscopic location. At 920, matching landmarks may be identified, including two or more landmarks in the target map that match respectively two or more landmarks in the real-time image. The matching landmarks may be identified based on a distance ratio between landmarks, as discussed above with reference to FIG. 7. At 930, The real-time image may be registered to the target map using the identified matching landmarks. The registration may include image transformation (e.g., translation, scaling, rotation, among others) and image alignment, as described above with reference to FIG. 7. At 940, endoscope tip may be localized and tracked based on the registration of the real-time image. Because the target map stores information of endoscopic tip locations with respect to a plurality of landmarks, the endoscopic tracker 330 may localize and track the endoscopic tip in real time throughout the procedure based on the landmarks on the registered image. For the target map that stores information about tissue types (e.g., normal or abnormal tissue at different target sites, such as indicted by the footprint of the aiming beam), the endoscopic tracker 330 may detect and track changes in tissue type over time at various sites of the target, or effectiveness of therapy delivered thereto.

Figure 10:
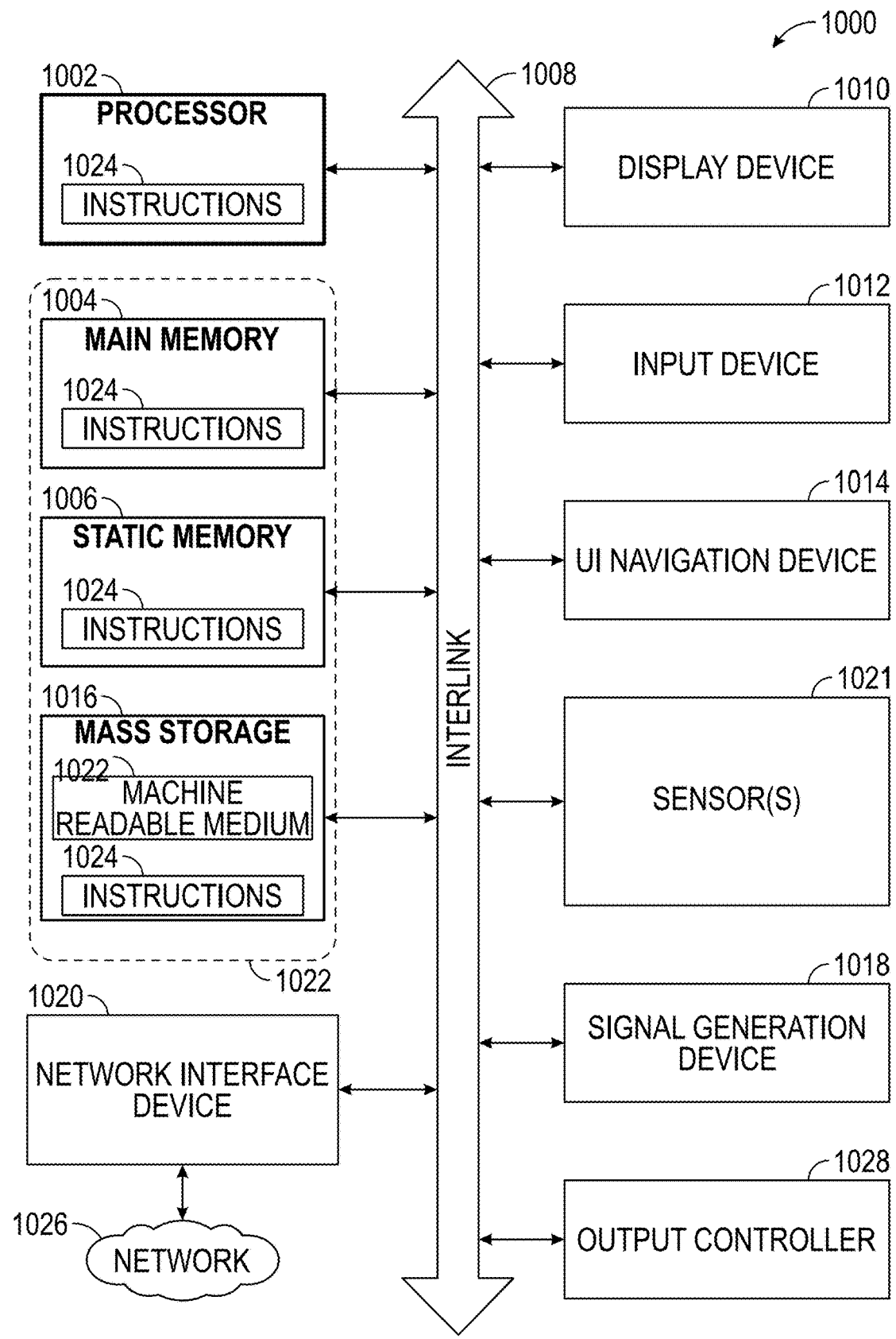
FIG. 10 is a block diagram illustrating an example machine upon which any one or more of the techniques (e.g., methodologies) discussed herein may perform.

FIG. 10 illustrates generally a block diagram of an example machine 1000 upon which any one or more of the techniques (e.g., methodologies) discussed herein may perform. Portions of this description may apply to the computing framework of various portions of the system 100, such as the endoscope controller 103.

In alternative embodiments, the machine 1000 may operate as a standalone device or may be connected (e.g., networked) to other machines. In a networked deployment, the machine 1000 may operate in the capacity of a server machine, a client machine, or both in server-client network environments. In an example, the machine 1000 may act as a peer machine in peer-to-peer (P2P) (or other distributed) network environment. The machine 1000 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, may include, or may operate by, logic or a number of components, or mechanisms. Circuit sets are a collection of circuits implemented in tangible entities that include hardware (e.g., simple circuits, gates, logic, etc.). Circuit set membership may be flexible over time and underlying hardware variability. Circuit sets include members that may, alone or in combination, perform specified operations when operating. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

Machine (e.g., computer system) 1000 may include a hardware processor 1002 (e.g., a central processing unit (CPU), a graphics processing unit (GPU), a hardware processor core, or any combination thereof), a main memory 1004 and a static memory 1006, some or all of which may communicate with each other via an interlink (e.g., bus) 1008. The machine 1000 may further include a display unit 1010 (e.g., a raster display, vector display, holographic display, etc.), an alphanumeric input device 1012 (e.g., a keyboard), and a user interface (UI) navigation device 1014 (e.g., a mouse). In an example, the display unit 1010, input device 1012 and UI navigation device 1014 may be a touch screen display. The machine 1000 may additionally include a storage device (e.g., drive unit) 1016, a signal generation device 1018 (e.g., a speaker), a network interface device 1020, and one or more sensors 1021, such as a global positioning system (GPS) sensor, compass, accelerometer, or other sensors. The machine 1000 may include an output controller 1028, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

The storage device 1016 may include a machine readable medium 1022 on which is stored one or more sets of data structures or instructions 1024 (e.g., software) embodying or utilized by any one or more of the techniques or functions described herein. The instructions 1024 may also reside, completely or at least partially, within the main memory 1004, within static memory 1006, or within the hardware processor 1002 during execution thereof by the machine 1000. In an example, one or any combination of the hardware processor 1002, the main memory 1004, the static memory 1006, or the storage device 1016 may constitute machine readable media.

While the machine-readable medium 1022 is illustrated as a single medium, the term "machine readable medium" may include a single medium or multiple media (e.g., a centralized or distributed database, and/or associated caches and servers) configured to store the one or more instructions 1024.

The term "machine readable medium" may include any medium that is capable of storing, encoding, or carrying instructions for execution by the machine 1000 and that cause the machine 1000 to perform any one or more of the techniques of the present disclosure, or that is capable of storing, encoding or carrying data structures used by or associated with such instructions. Non-limiting machine-readable medium examples may include solid-state memories, and optical and magnetic media. In an example, a massed machine-readable medium comprises a machine readable medium with a plurality of particles having invariant (e.g., rest) mass. Accordingly, massed machine-readable media are not transitory propagating signals. Specific examples of massed machine-readable media may include: non-volatile memory, such as semiconductor memory devices (e.g., Electrically Programmable Read-Only Memory (EPROM), Electrically Erasable Programmable Read-Only Memory (EPSOM)) and flash memory devices; magnetic disks, such as internal hard disks and removable disks; magneto-optical disks; and CD-ROM and DVD-ROM disks.

The instructions 1024 may further be transmitted or received over a communication network 1026 using a transmission medium via the network interface device 1020 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as WiFi®, IEEE 802.16 family of standards known as WiMax®), IEEE 802.15.4 family of standards, peer-to-peer (P2P) networks, among others. In an example, the network interface device 1020 may include one or more physical jacks (e.g., Ethernet, coaxial, or phone jacks) or one or more antennas to connect to the communication network 1026. In an example, the network interface device 1020 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 1000, and includes digital or analog communications signals or other intangible medium to facilitate communication of such software.

ADDITIONAL NOTES

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A system for endoscopic mapping of a target, the system comprising:
   an imaging system configured to capture an endoscopic image of the target, the endoscopic image including a footprint of an aiming beam directed at the target; and
   a video processor configured to:
      identifying one or more landmarks from the captured endoscopic image and determine their respective locations relative to the aiming beam footprint; and
      generate a target map by integrating a plurality of endoscopic images based on landmarks identified from one or more of the plurality of endoscopic images, wherein the plurality of endoscopic images include images of various sites of the target.

2. The system of claim 1, wherein the video processor is configured to identify a tissue type at a location of the aiming beam, and to mark the aiming beam footprint with a visual identifier indicating the identified tissue type.

3. The system of claim 1, comprising a spectrometer communicatively coupled to the video processor, the spectrometer configured to measure one or more spectroscopic properties of an illuminating light signal reflected from the target;
   wherein the video processor is configured to identify a tissue type at a location of the aiming beam based on the one or more spectroscopic properties, and to mark the aiming beam footprint with a visual identifier indicating the identified tissue type.

4. The system of claim 2, wherein the video processor is configured to identify the tissue type as normal tissue or abnormal tissue.

5. The system of claim 2, wherein the video processor is configured to mark the aiming beam footprint with different colors to indicate different tissue types.

6. The system of claim 1, wherein the video processor is configured to identify the one or more landmarks from the endoscopic image based on variation in brightness of pixels of the endoscopic image.

7. The system of claim 6, wherein the one or more landmarks are represented in the endoscopic image as a line segment or intersected line segments.

8. The system of claim 1, wherein the video processor is configured to:
   select, from the landmarks identified from one or more of the plurality of endoscopic images, a subset of landmarks based on whether laser energy is activated at respective target sites where the identified landmarks are located; and
   generate the target map by integrating the plurality of endoscopic images based on the selected subset of landmarks.

9. The system of claim 1, wherein the plurality of endoscopic images include images of various sites of the target including a first endoscopic image of a first target site captured from a first endoscopic location and a second endoscopic image of a second target site captured from a second endoscopic location, where the video processor is configured to:
   identify matching landmarks including two or more landmarks in the first endoscopic image that match corresponding two or more landmarks in the second endoscopic image;
   align the first and second endoscopic images with respect to the matching landmarks in a coordinate system of the first image; and
   generate the target map using at least the aligned first and second images.

10. The system of claim 9, wherein the video processor is configured to:
    transform the second image including one or more of a scaling, a translation, or a rotation of the second image; and
    align the transformed second image and the first image with respect to the matching landmarks.

11. The system of claim 10, wherein the transformation of the second image includes a matrix multiplication by a transformation matrix.

12. The system of claim 10, wherein the video processor is configured to scale the second image using a scaling factor based on a ratio of a distance between two of the matching landmarks in the first image to a distance between the corresponding two landmarks in the second image.

13. The system of claim 10, wherein the video processor is configured to scale the second image by a scaling factor based on a ratio of a geometric feature of an aiming beam footprint in the first image to a geometric feature of an aiming beam footprint in the second image.

14. The system of claim 10, wherein the video processor is configured to transform the second image to correct for a change in endoscopic orientations between the first and second images, the endoscopic orientation indicating a tilt of an endoscope tip with respect to a target site.

15. The system of claim 14, wherein the video processor is configured to detect the change in endoscopic orientation using a first slope between two of the matching landmarks in the first image and a second slope between the corresponding two landmarks in the second image.

16. The system of claim 14, wherein the video processor is configured to detect the change in endoscopic orientation using a first geometric feature of an aiming beam footprint in the first image and a second geometric feature of an aiming beam footprint in the second image.

17. The system of claim 16, wherein:
at least one of the first or second aiming beam footprint has an elliptical shape with a major axis and a minor axis; and
at least one of the first or the second geometric feature includes a ratio of a length of the major axis to a length of the minor axis.

18. The system of claim 1, comprising an endoscopic tracking system configured to:
from a real-time image of a procedure site of the target captured by the imaging system from an unknown endoscopic location during an endoscopic procedure, identify matching landmarks including two or more landmarks in the target map that match corresponding two or more landmarks in the real-time image;
register the real-time image to the target map using the matching landmarks; and
track endoscope tip location based on the registration of the real-time image.

19. The system of claim 18, wherein the endoscopic tracking system is configured to identify the matching landmarks based on one or more ratios of distances between landmarks in the real-time image and one or more ratios of distances between landmarks in the target map.

20. The system of claim 18, wherein the endoscopic tracking system is configured to generate an indication of a change in tissue type at a target site.

21. A method for endoscopic mapping of a target, the method comprising:
directing an aiming beam at a target;
capturing an endoscopic image of the target via an imaging system, the endoscopic image including a footprint of the aiming beam;
identifying, via a video processor, one or more landmarks from the captured endoscopic image, and determining respective locations of the one or more landmarks relative to the aiming beam footprint; and
generating, via the video processor, a target map by integrating a plurality of endoscopic images based on landmarks identified from one or more of the plurality of endoscopic images, wherein the plurality of endoscopic images include images of various sites of the target.

22. The method of claim 21, comprising:
identifying a tissue type at a location of the aiming beam using an illuminating light signal reflected from the target; and
marking the aiming beam footprint with a visual identifier indicating the identified tissue type.

23. The method of claim 21, wherein identifying the one or more landmarks from the endoscopic image is based on variation in brightness of pixels of the endoscopic image.

24. The method of claim 21, wherein the plurality of endoscopic images include images of various sites of the target including a first endoscopic image of a first target site captured at a first endoscopic location and a second endoscopic image of a second target site captured at a second endoscopic location, the method comprising:
identifying matching landmarks including two or more landmarks in the first endoscopic image that match corresponding two or more landmarks in the second endoscopic image;
aligning the first and second endoscopic images with respect to the matching landmarks in a coordinate system of the first image; and
generating the target map using at least the aligned first and second images.

25. The method of claim 24, wherein aligning the first and second endoscopic images includes:
transforming the second image including one or more of a scaling, a translation, or a rotation of the second image; and
aligning the transformed second image and the first image with respect to the matching landmarks.

26. The method of claim 25, wherein transforming the second image includes scaling the second image by a scaling factor based on a ratio of a distance between two of the matching landmarks in the first image to a distance between the two corresponding landmarks in the second image.

27. The method of claim 25, wherein transforming the second image includes scaling the second image by a scaling factor based on a ratio of a geometric feature of an aiming beam footprint in the first image to a geometric feature of an aiming beam footprint in the second image.

28. The method of claim 25, wherein transforming the second image includes correcting for a change in endoscopic orientation between the first and second images, the endoscopic orientation indicating a tilt of an endoscope tip with respect to a target site.

29. The method of claim 21, further comprising:
capturing a real-time image of a procedure site of the target using the imaging system from an unknown endoscopic location during an endoscopic procedure;
identifying matching landmarks including two or more landmarks in the target map that match corresponding two or more landmarks in the real-time image;
registering the real-time image to the target map using the matching landmarks; and
tracking endoscope tip location based on the registration of the real-time image.

30. The method of claim 29, wherein identifying matching landmarks is based on one or more ratios of distances between landmarks in the real-time image and one or more ratios of distances between landmarks in the target map.

* * * * *